US008389442B2

(12) United States Patent
Ackermann et al.

(10) Patent No.: US 8,389,442 B2
(45) Date of Patent: Mar. 5, 2013

(54) N-PHENYL-'(4-PYRIDYL)-AZINYL!AMINE DERIVATIVES AS PLANT PROTECTION AGENTS

(75) Inventors: Peter Ackermann, Basel (CH); Daniel Stierli, Basel (CH); Martin Diggelmann, Berkshire (CH); Fredrik Cederbaum, Basel (CH); Jean Wenger, Basel (CH); Ruud Titulaer, Nijmegen (NL)

(73) Assignee: Syngenta Crop Protection LLC, Greensboro, NC (US)

( * ) Notice: Subject to any disclaimer, the term of this patent is extended or adjusted under 35 U.S.C. 154(b) by 1821 days.

(21) Appl. No.: 10/549,486

(22) PCT Filed: Mar. 25, 2004

(86) PCT No.: PCT/IB2004/001075
§ 371 (c)(1),
(2), (4) Date: Aug. 3, 2006

(87) PCT Pub. No.: WO2004/084634
PCT Pub. Date: Oct. 7, 2004

(65) Prior Publication Data
US 2007/0032490 A1 Feb. 8, 2007

(30) Foreign Application Priority Data
Mar. 28, 2003 (GB) .................................. 0307268.3

(51) Int. Cl.
*A01N 43/66* (2006.01)
*A01N 43/54* (2006.01)
*A01N 43/40* (2006.01)
*C07D 403/00* (2006.01)
*C07D 251/00* (2006.01)
*C07D 237/00* (2006.01)
*C07D 237/02* (2006.01)
*C07D 213/04* (2006.01)

(52) U.S. Cl. ........ 504/230; 504/239; 504/251; 544/212; 544/323; 544/324; 546/255

(58) Field of Classification Search ........................ None
See application file for complete search history.

(56) References Cited

FOREIGN PATENT DOCUMENTS

| WO | WO 95/09847 A | 4/1995 |
|---|---|---|
| WO | WO 95/09851 A | 4/1995 |
| WO | WO 95/09853 A | 4/1995 |
| WO | WO9509853 * | 4/1995 |
| WO | WO 01/25220 A | 4/2001 |
| WO | WO 01/93682 A | 12/2001 |
| WO | WO 02/053560 A | 7/2002 |
| WO | WO02053560 A * | 7/2002 |
| WO | WO 03/047347 A | 6/2003 |
| WO | WO 2004/009562 A | 1/2004 |

* cited by examiner

*Primary Examiner* — Alton Pryor
(74) *Attorney, Agent, or Firm* — R. Kody Jones

(57) ABSTRACT

The use of fungicidal compounds of formula $I_j$ wherein A and A' are both N or A and A' are both CH or A is CH and A' is N; j is 0 or 1 and the R groups are as defined in claim 1; their preparation and compositions 10 comprising the compounds.

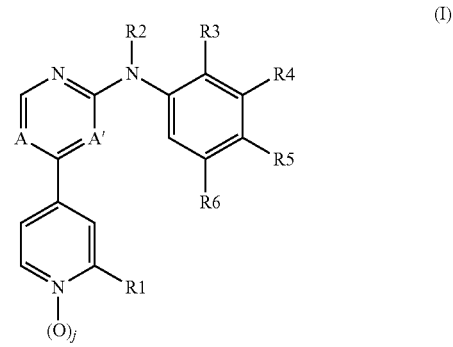

(I)

18 Claims, No Drawings

N-PHENYL-'(4-PYRIDYL)-AZINYL!AMINE DERIVATIVES AS PLANT PROTECTION AGENTS

This application is a 371 of International Application No. PCT/IB2004/001075 filed Mar. 25, 2004, which claims priority to GB0307268.3, filed Mar. 28, 2003, the contents of which are incorporated herein by reference.

The present invention relates to N-phenyl-[(4-pyridyl)-azinyl]-amine derivatives, to a method of protecting plants against attack or infestation by phytopathogenic organisms, such as nematodes or insects or especially microorganisms, preferably fungi, bacteria and viruses, or combinations of two or more of these organisms, by applying a N-phenyl-[(4-pyridyl)-azinyl]-amine derivative as specified hereinafter to a part and/or to the site of a plant, to the use of said derivative for protecting plants against said organisms, and to compositions comprising said derivative as the active component. The invention further relates to the preparation of these N-phenyl-[(4-pyridyl)-azinyl]-amine derivatives.

Certain N-phenyl-4-(4-pyridyl)-2-pyrimidineamine derivatives are disclosed in WO 01/93682, WO 02/053560 and WO03/047347 as plant protection agents.

It has now been found that the certain N-phenyl-[(4-pyridyl)-azinyl]-amines are effective in plant protection and related areas, showing advantageous properties in the treatment of plant diseases caused by organisms.

There is therefore provided a method of controlling and preventing an infestation of crop plants by phytopathogenic microorganisms, which comprises the application to the plant or parts of plants or to the locus thereof as active ingredient an N-phenyl-[(4-pyridyl)-azinyl]-amine derivative of the formula I

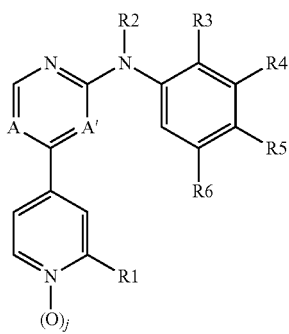

wherein
A and A' are both N or A and A' are both CH or A is CH and A' is N;
j is 0 or 1
$R_1$ is
a) hydrazino, that is unsubstituted or one- to threefold substituted by optionally substituted alkyl and/or optionally substituted acyl,
b) cyclohexylamino, tetrahydro-4H-pyranyl-4-amino, pyrrolidine-3-amino, 2- or 3-tetrahydro-furylamino, all optionally substituted by amino, hydroxy, alkoxy, alkyl or alkoxyalkyl,
c) piperazinyl that is optionally substituted by amino, amino-lower alkyl, hydroxy, alkoxy, alkyl or alkoxyalkyl,
d) morpholinyl that is optionally substituted by amino, amino-lower alkyl, hydroxy, alkoxy, alkyl or alkoxyalkyl,
e) amino or mono- or di-(lower alkyl)amino wherein the lower alkyl moieties are unsubstituted or substituted by one or more (preferably 1 to 3, especially 1 or 2) substituents independently selected from the group consisting of unsubstituted amino, N-mono- or N,N-di-(lower alkyl)-amino, (lower alkoxy)-lower alk-oxy, lower alkoxycarbonylamino, hydroxy-lower alkoxycarbonylamino, lower alkoxy-lower alkoxycarbonylamino, morpholinyl, hydroxy-lower alkylamino, cyano, halogen, oxo, hydroximino, alkoximino, optionally substituted hydrazono, lower alkenyl, lower alkynyl, guanidyl, lower alkanoylamino, hydroxy-lower alkanoylamino, lower alkoxy-lower alkanoylamino, halo-lower alkanoylamino, lower alkylaminocarbonylamino, hydroxy-lower alkylaminocarbonylamino, lower alkoxy-lower alkylaminocarbonylamino, amidino, di-lower-alkylamino-cyclohexyl, carboxy, lower alkoxycarbonyl, hydroxy-lower alkoxycarbonyl, lower alkoxy-lower alkoxycarbonyl, lower alkylcarbonyldioxy (=lower alkoxycarbonyloxy), hydroxy-lower alkoxycarbonyloxy, lower alkoxy-lower alkoxycarbonyloxy, lower alkanoyloxy, halo-lower alkanoyloxy, hydroxy-lower alkanoyloxy, lower alkoxy-lower alkanoyloxy, carbamoyl, N-mono- or N,N-di-lower alkylcarbamoyl, N-(hydroxy-lower alkyl)carbamoyl, N-lower alkyl-N-hydroxy-lower alkyl-carbamoyl, N,N-di-(hydroxy-lower alkyl)-carbamoyl, N-hydroxy-carbamoyl, hydroxy, lower alkoxy, lower alkenyloxy, lower alkinyloxy, lower haloalkoxy, lower alkylthio, lower alkylsulfoxyl, lower alkylsulfonyl, lower alkoxysilyl, 4tetrahydro-4H-pyranyl, 3-pyrrolidinyl, 2- or 3-tetrahydrofuryl, 2- or 3-dihydrofuryl piperazinyl, lower alkanoyl-piperazinyl (including formylpiperazinyl), optionally substituted heteroaryl and optionally substituted heteroaryloxy,
f) optionally substituted alkanoylamino, optionally substituted alkenoylamino, optionally substituted alkynoylamino, optionally substituted mono- or di-alkylaminocarbonylamino, optionally substituted alkoxycarbonylamino, optionally substituted mono- or di-alkylaminosulfonylamino, optionally substituted mono- or di-alkylaminosulfoxylamino,
g) N-(optionally substituted alkyl)-N-(optionally substituted lower alkanoyl)-amino,
h) N-(optionally substituted alkyl)-N-(optionally substituted alkoxycarbonyl)-amino,
i) N-(optionally substituted alkyl)-N-(N',N'-mono- or di-[optionally substituted alkyl]-aminocarbonyl)-amino,
j) N=C($R_7,R_8$) wherein $R_7$ is hydrogen, alkyl, amino, mono- or di-alkylamino and $R_8$ is amino, mono- or dialkylamino or wherein $R_7$ and $R_8$, together with the binding carbon atom, form a saturated five- to seven-membered ring with 0, 1 or 2 ring nitrogen atoms that is optionally substituted by one or more substituents, preferably 1 to 3 substituents, especially lower alkyl,
k) an optionally substituted 4 to 7 membered heterocyclyl group containing one or two nitrogen, oxygen or sulfur atoms but at least one nitrogen atom through which the heterocyclyl ring is attached to the remainder of the molecule;
$R_2$ is hydrogen, $C_1$-$C_4$-alkyl, $C_3$-$C_4$-alkenyl, $C_3$-$C_4$-alkynyl, —$CH_2OR_{16}$, —$CH_2SR_{16}$, —$C(O)R_{16}$, —$C(O)OR_{16}$, $SO_2R_{16}$, $SOR_{16}$ or $SR_{16}$; where $R_{16}$ is $C_1$-$C_8$-alkyl, $C_1$-$C_8$-alkoxyalkyl, $C_1$-$C_8$ haloalkyl or phenyl$C_1$-$C_2$-alkyl, wherein the phenyl may be substituted by up to three groups selected from halo or $C_1$-$C_4$-alkyl;
$R_3$ is hydrogen, halogen, $C_1$-$C_4$alkyl, $C_1$-$C_4$haloalkyl, $C_1$-$C_4$haloalkoxy; hydroxy, mercapto, cyano or $C_1$-$C_4$alkoxy;

$R_4$, $R_5$ and $R_6$ are independently of each other hydrogen, halogen, optionally substituted alkyl, optionally substituted alkenyl, optionally substituted alkynyl, optionally substituted aryl, optionally substituted heteroaryl, optionally substituted alkoxy, optionally substituted acyloxy, optionally substituted alkenyloxy, optionally substituted alkynyloxy, optionally substituted aryloxy, optionally substituted heteroaryloxy, optionally substituted acylamino, optionally substituted thioalkyl, $COOR_{17}$, $CONR_{18}R_{19}$, $S(O)_kR_{20}$, $SO_2NR_{21}R_{22}$, $NR_{23}R_{24}$, $NR_{25}SO_2R_{26}$, $NO_2$, CN, $C(=O)R_{27}$, $C(=NOR_{28})R_{29}$ or $R_4$ and $R_5$ or $R_5$ and $R_6$ together form a five to six-membered saturated or unsaturated carbocyclic ring system or ring system or a five to six-membered heteroaromatic or heterocyclic ring system which is optionally substituted and contains one to three heteroatoms selected from O, N or S;

k is 0, 1 or 2 and $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$ and $R_{29}$ are independently H or optionally substituted alkyl or optionally substituted aryl; or a salt thereof provided that when A is CH, A' is N and $R_3$, $R_5$ and $R_6$ are all H then $R_4$ is not hydrogen, halogen, alkoxy, haloalkyl, haloalkoxy or alkyl; and that when A is CH and A' is N then $R_1$ is not an optionally substituted N-linked 5- or 6-membered heterocyclyl group containing two adjacent nitrogen atoms as the only heteroatoms in the heterocycyclic ring.

The compounds of formula (I) are preferably compounds of formula IA wherein A, A', j, $R_1$, $R_2$ and $R_3$ are as defined in relation to formula (I) and $R_4$, $R_5$ and $R_6$ are independently of each other hydrogen, halogen, optionally substituted alkyl, optionally substituted alkenyl, optionally substituted alkynyl, optionally substituted alkoxy, optionally substituted acyloxy, optionally substituted alkenyloxy, optionally substituted alkynyloxy, optionally substituted acylamino, optionally substituted thioalkyl, $COOR_{17}$, $CONR_{18}R_{19}$, $S(O)_kR_{20}$, $SO_2NR_{21}R_{22}$, $NR_{23}R_{24}$, $NR_{25}SO_2R_{26}$, $NO_2$, CN, $C(=O)R_{27}$, $C(=NOR_{28})R_{29}$ or $R_4$ and $R_5$ or $R_5$ and $R_6$ together form a five to six-membered saturated or unsaturated carbocyclic ring system or ring system or a five to six-membered heteroaromatic or heterocyclic ring system which is optionally substituted and contains one to three heteroatoms selected from O, N or S; k is 0, 1 or 2 and $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$ and $R_{29}$ are independently H or optionally substituted alkyl or optionally substituted aryl.

In the context of the present specification alkyl as a group per se and as a structural element of hydroxyalkyl, thioalkyl, alkoxy, alkenyl, alkenyloxy, alkynyl alkynyloxy or haloalkoxy—is preferably $C_1$-$C_6$-alkyl, more preferably lower alkyl, and is linear i.e. methyl, ethyl, propyl, butyl, pentyl or hexyl, or branched, e.g. isopropyl, isobutyl, sec.-butyl, tert.-butyl, isopentyl, neopentyl or isohexyl. Lower alkyl is preferably methyl or ethyl.

Specific examples of alkenyl and alkynyl include alkyl, 2-butenyl, 3-butenyl, propargyl, 2-butynyl and 3 butynyl.

When present, the optional substituents on an alkyl, alkenyl or alkynyl moiety include one or more of halogen, nitro, cyano, oxo (and acetals and ketals formed therefrom), $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{3-10}$ alkoxy, $C_{3-10}$ alkoxy($C_{3-10}$)alkoxy, $C_{1-6}$ alkoxy-carbonyl($C_{3-10}$)alkoxy, $C_{3-10}$ haloalkoxy, phenyl($C_{1-4}$)alkoxy (where the phenyl group is optionally substituted by one or more of $C_{1-6}$ alkyl, $C_{1-6}$ alkoxy, $C_{1-6}$ haloalkyl, CN, nitro or halogen), $C_{3-7}$ cycloalkyloxy (where the cycloalkyl group is optionally substituted with $C_{1-6}$ alkyl or halogen), $C_{3-10}$ alkenyloxy, $C_{3-10}$ alkynyloxy, SH, $C_{3-10}$ alkylthio, $C_{3-10}$ haloalkylthio, phenyl($C_{1-4}$)-alkylthio (where the phenyl group is optionally substituted by one or more of $C_{1-6}$ alkyl, $C_{1-6}$ alkoxy, $C_{1-6}$ haloalkyl, CN, nitro or halogen), $C_{3-7}$ cycloalkylthio (where the cycloalkyl group is optionally substituted with $C_{1-6}$ alkyl or halogen), tri($C_{1-4}$)-alkylsilyl($C_{1-6}$)alkylthio, phenylthio (where the phenyl group is optionally substituted by one or more of $C_{1-6}$ alkyl, $C_{1-6}$ alkoxy, $C_{1-6}$ haloalkyl, CN, nitro or halogen), $C_{1-6}$ alkylsulfonyl, $C_{1-6}$ haloalkylsulfonyl, $C_{1-6}$ alkylsulfinyl, $C_{1-6}$ haloalkylsulfinyl, phenylsulfonyl (where the phenyl group is optionally substituted by one or more of $C_{1-6}$ alkyl, $C_{1-6}$ alkoxy, $C_{1-6}$ haloalkyl, CN, nitro or halogen), tri($C_{1-4}$)alkylsilyl, phenyldi-($C_{1-4}$)alkylsilyl, ($C_{1-4}$)alkyldiarylsilyl, triphenylsilyl, $C_{3-10}$ alkylcarbonyl, $HO_2C$, $C_{3-10}$ alkoxycarbonyl, aminocarbonyl, $C_{1-6}$ alkylaminocarbonyl, di($C_{1-6}$ alkyl)-aminocarbonyl, N—($C_{1-3}$ alkyl)-N—($C_{1-3}$ alkoxy)aminocarbonyl, $C_{1-6}$ alkylcarbonyloxy, phenylcarbonyloxy (where the phenyl group is optionally substituted by one or more of $C_{1-6}$ alkyl, $C_{1-6}$ alkoxy, $C_{1-6}$ haloalkyl, CN, nitro or halogen), di($C_{1-6}$)alkylaminocarbonyloxy, phenyl (itself optionally substituted by one or more of $C_{1-6}$ alkyl, $C_{1-6}$ alkoxy, $C_{1-6}$ haloalkyl, CN, nitro or halogen), naphthyl (itself optionally substituted by $C_{1-6}$ alkyl or halogen), heteroaryl (itself optionally substituted by $C_{1-6}$ alkyl or halogen), heterocyclyl (itself optionally substituted with $C_{1-6}$ alkyl or halogen), phenyloxy (where the phenyl group is optionally substituted by one or more of $C_{1-6}$ alkyl, $C_{1-6}$ alkoxy, $C_{1-6}$ haloalkyl, CN, nitro or halogen), naphthyloxy (where the naphthyl group is optionally substituted by $C_{1-6}$ alkyl or halogen), heteroaryloxy, (where the heteroaryl group is optionally substituted by $C_{1-6}$ alkyl or halogen), heterocyclyloxy (where the heterocyclyl group is optionally substituted with $C_{1-6}$ alkyl or halogen), amino, $C_{1-6}$ alkylamino, di-($C_{1-6}$) alkylamino, $C_{1-6}$ alkylcarbonylamino and N—($C_{1-6}$)alkylcarbonyl-N—($C_{1-6}$)-alkylamino.

Preferred substituents on an alkyl, alkenyl or alkynyl moiety include one or more of halogen, nitro, cyano, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{3-10}$ alkoxy, $C_{3-10}$ alkoxy ($C_{3-10}$)alkoxy, $C_{1-6}$ alkoxy-carbonyl($C_{3-10}$)alkoxy, $C_{3-10}$ haloalkoxy, phenyl($C_{1-4}$)alkoxy (where the phenyl group is optionally substituted by $C_{1-6}$ alkyl or halogen), $C_{3-7}$ cycloalkyloxy (where the cycloalkyl group is optionally substituted with $C_{1-6}$ alkyl or halogen), $C_{3-10}$ alkenyloxy, $C_{3-10}$ alkynyloxy, SH, $C_{3-10}$ alkylthio, $C_{3-10}$ haloalkylthio, phenyl ($C_{1-4}$)alkylthio (where the phenyl group is optionally substituted by $C_{1-6}$ alkyl or halogen), $C_{3-7}$ cycloalkylthio (where the cycloalkyl group is optionally substituted with $C_{1-6}$ alkyl or halogen), tri($C_{1-4}$)alkylsilyl($C_{1-6}$)alkylthio, phenylthio (where the phenyl group is optionally substituted by $C_{1-6}$ alkyl or halogen), $C_{1-6}$ alkylsulfonyl, $C_{1-6}$ haloalkylsulfonyl, $C_{1-6}$ alkylsulfinyl, $C_{1-6}$ haloalkylsulfinyl, phenylsulfonyl (where the phenyl group is optionally substituted by $C_{1-6}$ alkyl or halogen), tri($C_{1-4}$)alkylsilyl, phenyldi($C_{1-4}$)alkylsilyl, ($C_{1-4}$)alkyldiarylsilyl, triphenylsilyl, $C_{3-10}$ alkylcarbonyl, $HO_2C$, $C_{3-10}$ alkoxycarbonyl, aminocarbonyl, $C_{1-6}$ alkylaminocarbonyl, di($C_{1-6}$ alkyl)-aminocarbonyl, N—($C_{1-3}$ alkyl)-N—($C_{1-3}$ alkoxy)aminocarbonyl, $C_{1-6}$ alkylcarbonyloxy, phenylcarbonyloxy (where the phenyl group is optionally substituted by $C_{1-6}$ alkyl or halogen), di($C_{1-6}$)alkylaminocarbonyloxy, phenyl (itself optionally substituted by $C_{1-6}$ alkyl or halogen), heteroaryl (itself optionally substituted by $C_{1-6}$ alkyl or halogen), heterocyclyl (itself optionally substituted with $C_{1-6}$ alkyl-or halogen), phenyloxy (where the phenyl group is optionally substituted by $C_{1-6}$ alkyl or halogen), heteroaryloxy, (where the heteroaryl group is optionally substituted by $C_{1-6}$ alkyl or halogen), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino and N—($C_{1-6}$)alkylcarbonyl-N—($C_{1-6}$) alkylamino.

More preferred substituents on an alkyl, alkenyl and alkynyl moiety include one or more of halogen, nitro, cyano, $C_{3-7}$ cycloalkyl (itself optionally substituted with $C_{1-6}$ alkyl or halogen), hydroxy, $C_{3-10}$ alkoxy, $C_{3-10}$ alkoxy($C_{3-10}$)alkoxy, $C_{1-6}$ alkoxy-carbonyl($C_{3-10}$)alkoxy, $C_{3-10}$ haloalkoxy, SH, $C_{3-10}$ alkylthio, $C_{3-10}$ haloalkylthio, $C_{1-6}$ alkylsulfonyl, $C_{1-6}$ haloalkylsulfonyl, $C_{1-6}$ alkylsulfinyl, $C_{1-6}$ haloalkylsulfinyl, phenylsulfonyl (where the phenyl group is optionally substituted by $C_{1-6}$ alkyl or halogen), $HO_2C$, $C_{3-10}$ alkoxycarbonyl, aminocarbonyl, $C_{1-6}$ alkylaminocarbonyl, heteroaryl (itself optionally substituted by $C_{1-6}$ alkyl or halogen), heterocyclyl (itself optionally substituted with $C_{1-6}$ alkyl or halogen), phenyloxy (where the phenyl group is optionally substituted by $C_{1-6}$ alkyl or halogen), amino, $C_{1-6}$ alkylamino and di($C_{1-6}$) alkylamino.

Aryl includes naphthyl, anthracyl, fluorenyl and indenyl but is preferably phenyl.

The term heteroaryl and heteroaromatic refer to an aromatic ring containing up to 10 atoms including one or more heteroatoms (preferably one or two heteroatoms) selected from O, S and N. Examples of such rings include benzimidazolyl, benzisoxazolyl, benzisothiazolyl, benzocoumarinyl, benzofuryl, benzothiadiazolyl, benzothiazolyl, benzothienyl, benzoxazolyl, benzoxdiazolyl, quinazolinyl, quinolyl, quinoxalinyl, carbazolyl, dihydrobenzofuryl, furyl (especially 2- or 3-furyl), imidazolyl (especially 1-imidazolyl), indazolyl, indolyl, isoquinolinyl, isothiazolyl, isoxazolyl, methylenedioxyphenyl, ethylenedioxyphenyl, naphthyridinyl, oxazolyl, phenanthridinyl, phthalazinyl, pteridinyl, purinyl, pyrazinyl, pyrazolyl, pyridazinyl, pyrazolo[3,4-b]-pyridyl, pyridyl (especially 2-, 3- or 4-pyridyl), pyrimidyl, pyrrolyl, tetrazolyl (especially tetrazol-1-yl), oxadiazolyl, thiadiazolyl, thiazolyl (especially 2-, 4- or 5-thiazolyl), thienyl (especially 2- or 3-thienyl), triazinyl (especially 1,3,5-triazinyl) and triazolyl (especially 1,2,4-triazol-1-yl). Pyridine, pyrimidine, furan, quinoline, quinazoline, pyrazole, thiophene, thiazole, oxazole and isoxazole are preferred.

The terms heterocycle and heterocyclyl refer to a non-aromatic ring containing up to 10 atoms including one or more (preferably one or two) heteroatoms selected from O, S and N. Examples of such rings include 1,3-dioxolane, tetrahydrofuran and morpholine.

When present, the optional substituents on heterocyclyl include $C_{1-6}$ alkyl as well as those optional substituents given above for an alkyl moiety.

Carbocyclic rings include aryl, cycloalkyl and cycloalkenyl rings.

Cycloalkyl includes cyclopropyl, cyclopentyl and cyclohexyl.

Cycloalkenyl includes cyclopentenyl and cyclohexenyl.

When present, the optional substituents on heteroaryl and aryl rings are selected, independently, from halogen, nitro, cyano, NCS—, $C_{1-6}$ alkyl, $C_{1-6}$ haloalkyl, $C_{1-6}$ alkoxy-($C_{1-6}$) alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy ($C_{1-10}$)alkoxy, tri($C_{1-4}$)alkyl-silyl($C_{1-6}$)alkoxy, $C_{1-6}$ alkoxy-carbonyl($C_{1-10}$)alkoxy, $C_{1-10}$ haloalkoxy, aryl($C_{1-4}$)alkoxy (where the aryl group is optionally substituted), $C_{3-7}$ cycloalkyloxy (where the cycloalkyl group is optionally substituted with $C_{1-6}$ alkyl or halogen), $C_{1-10}$ alkenyloxy, $C_{1-10}$ alkynyloxy, SH, $C_{1-10}$-alkylthio, $C_{1-10}$ haloalkylthio, aryl($C_{1-4}$)alkylthio (where the aryl group may be further optionally substituted), $C_{3-7}$ cycloalkylthio (where the cycloalkyl group is optionally substituted with $C_{1-6}$ alkyl or halogen), tri($C_{1-4}$)-alkylsilyl($C_{1-6}$)alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group is optionally substituted), tri($C_{1-4}$)alkylsilyl, aryldi-($C_{1-4}$)alkylsilyl, ($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)aminocarbonyl, N—($C_{1-3}$ alkyl)-N—($C_{1-3}$ alkoxy)aminocarbonyl, $C_{1-6}$ alkylcarbonyloxy, arylcarbonyloxy (where the aryl group is optionally substituted), di($C_{1-6}$)alkylamino-carbonyloxy, aryl (itself optionally substituted), heteroaryl (which itself may be further optionally substituted), heterocyclyl (itself optionally substituted with $C_{1-6}$ alkyl or halogen), aryloxy (where the aryl group is optionally substituted), heteroaryloxy (where the heteroaryl group is optionally substituted), heterocyclyloxy (where the heterocyclyl group is optionally substituted with $C_{1-6}$ alkyl or halogen), amino, $C_{1-6}$ alkylamino, di-($C_{1-6}$)alkylamino, $C_{1-6}$ alkylcarbonylamino and N—($C_{1-6}$)alkylcarbonyl-N—($C_{1-6}$)-alkylamino.

For substituted phenyl amd heteroaryl moieties it is preferred that one or more substituents are independently selected from halogen, $C_{1-6}$ alkyl, $C_{1-6}$ haloalkyl, $C_{1-6}$ alkoxy ($C_{1-6}$)alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, $CO_2H$, $C_{1-6}$ alkylcarbonyl, $C_{1-6}$ alkoxycarbonyl, $R_{33}R_{34}N$ or $R_{35}R_{36}NC(O)$; wherein $R_{33}$, $R_{34}$, $R_{35}$ and $R_{36}$ are, independently, hydrogen or $C_{1-6}$ alkyl.

In the context of the specification the term halogen is fluorine, bromine, iodine or preferably chlorine; similarly haloalkyl is preferably $C_1$-$C_6$-alkyl, more preferably lower alkyl, that is linear or branched and is substituted by one or more, for example in the case of halo-ethyl up to five, halogen atoms, especially fluorine (an example is trifluoromethyl.

Haloalkoxy is preferably $C_1$-$C_6$-alkoxy, more preferably lower alkoxy, that is linear or branched and that is substituted by one or more, for example in the case of halo-ethyl up to five, halogen atoms, especially fluorine; trifluoromethoxy and 1,1,2,2-tetrafluoroethoxy are especially preferred.

Acyl is preferably $C_1$-$C_{16}$ alkanoyl, more preferably lower alkanoyl, and is linear or branched. Lower alkanoyl is preferably formyl, acetyl or in a broader sense of the invention propionyl or butyryl.

The compounds of formula I can form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid, oxalic acid or amino acids, such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or: cinnamic acid, heteroaromatic carboxylic acids, such as nicotinic acid or isonicotinic acid, aliphatic sulfonic acids, such as methane-, ethane- or 2-hydroxy-ethane-sulfonic acid, or aromatic sulfonic acids, for example benzene-, p-toluene- or naphthalene-2-sulfonic acid.

The pyridine-N-oxides of formula I can form acid addition salts with strong acids, such as hydrochloric acid, nitric acid, phosphoric acid or sulfonic acids, such as benzenesulfonic acid.

Formula I according to the invention shall include all the possible isomeric forms, as well as mixtures, e.g. racemic mixtures, and any mixtures of rotamers.

In view of the close relationship between the compounds of formula I in free form and in the form of their salts, including also salts that can be used as intermediates, for example in the purification of the compounds of formula I or in order to identify those compounds, herein-before and hereinafter any reference to the (free) compounds is to be understood as including also the corresponding salts, where appropriate and expedient.

Among the compounds of formula I according to the present invention the following groups of compounds are preferred. These groups are in any combination those wherein j is 0;

$R_1$ is hydrazino substituted by one to three substituents independently selected from the group consisting of $C_{1-4}$ alkyl, $C_{1-4}$ haloalkyl, $C_{1-4}$ hydroxyalkyl, $C_{1-4}$ alkoxy$C_{1-4}$ alkyl and $C_{1-4}$acyl; or $R_1$ is cyclohexyl-amino substituted by amino; or $R_1$ is piperazinyl optionally substituted by one or two $C_{1-4}$ alkyl, acyl or $C_{1-4}$ aminoalkyl groups; or $R_1$ is morpholinyl optionally substituted by one or two $C_{1-4}$ alkyl, acyl or $C_{1-4}$ aminoalkyl groups; mono- or di-(lower alkyl)-amino; or $R_1$ is mono- or di-(lower alkyl)-amino where the lower alkyl moieties are independently substituted by N-mono- or N,N-di-(lower alkyl)amino, (lower alkoxy)-lower alkoxy, caboxy-lower alkyl, lower alkoxy, hydroxy, hydroxy-lower alkylamino, lower alkylamino-carbonylamino or lower alkoxycarbonylamino or $C_{1-8}$ alkoximino; or $R_1$ is $N=CR_7R_8$ where $R_7$ and $R_8$ together with the carbon atom to which they are attached form a five- to seven-membered ring with 2 ring nitrogen atoms adjacent to the carbon atom double bonded to the external N atom; or $R_1$ is the moiety

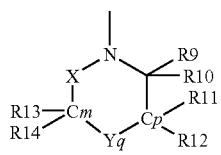

wherein
the sum of (m+p) together is 0, 1, 2 or 3;
q is 0 or 1, and the sum of (m+p+q) together is 1, 2, 3 or 4;
$R_9$ is hydrogen, $C_1$-$C_6$-alkyl, $C_1$-$C_6$-haloalkyl or $C_1$-$C_6$-alkoxy,
$R_{10}$ is hydrogen, $C_1$-$C_6$-alkyl, $C_3$-$C_4$-alkenyl or $C_3$-$C_4$-alkynyl;
each of $R_{11}$, $R_{12}$, $R_{13}$ and $R_{14}$ is, independently of the others, hydrogen, $C_1$-$C_6$-alkyl,
$C_1$-$C_6$-haloalkyl, hydroxy-$C_1$-$C_6$-alkyl or $C_1$-$C_6$-alkoxy-$C_1$-$C_6$-alkyl, or the ring members
$CR_{13}R_{14}$ or $CR_{11}R_{12}$ or $CR_9R_{10}$ are independently of each other a carbonyl group (C=O) or a group C=S;
X is C=O, C=S, S=O or O=S=O;
Y is O, S, C=O, $CH_2$, —N($R_{15}$)—, —O—N($R_{15}$)—, —N($R_{15}$)—O— or —NH—; and
$R_{15}$ is $C_1$-$C_8$-alkyl, $C_1$-$C_8$-alkoxyalkyl, $C_1$-$C_8$ haloalkyl or phenyl$C_1$-$C_2$-alkyl wherein the phenyl may be substituted by up to three groups selected from halo or $C_1$-$C_4$-alkyl; or $R_1$ is hydrazino substituted by a lower alkyl, trifluoromethyl, 2-hydroxyethyl, hydroxymethyl, 1-hydroxymethyl-n-propyl, 2-methoxyethyl, ethoxymethyl, or 1-methoxymethyl-n-propyl group and especially by 2-hydroxyethyl group; or $R_1$ is 2- or 4-amino-cyclohexyl-amino; or
$R_1$ is 4-(2-amino-ethyl)-piperazin-1-yl; or
$R_1$ is 4-formyl-piperazinyl; or
$R_1$ is 4-morpholinyl; or
$R_1$ is 2-morpholin-4-yl-ethylamino, 3-lower alkyl- or 3,5-di (lower alkyl)morpholino, especially 3-methyl- or 3,5-dimethylmorpholino; or $R_1$ is dimethylamino, 3-(dimethylamino)-1-methyl-n-propylamino, 2-amino-ethylamino, 3-amino-n-propylamino, N-(methoxymethyl)-N-{2-[(methoxy)-methoxy]-1-methyl-ethyl}-amino, 2-hydroxy-ethylamino, 3-(2-hydroxy-ethyl-amino)-prop-1-ylamino, methylamino-carbonyl-amino, 2- or 3-hydroxy-n-propylamino, 1,1-dimethyl-3-hydroxy-n-propylamino, 1-n-propyl-2-hydroxy-ethylamino, 1,1-dimethyl-2-hydroxy-ethylamino, 1-ethyl-2-hydroxy-ethylamino, 2-hydroxy-1-(hydroxymethyl)-ethylamino, 2-hydroxy-1-methyl-ethylamino, 2-hydroxy-1-(sec-butyl)-ethylamino, 2-methoxy-ethylamino, 1-ethyl-2-methoxy-ethylamino, 2-methoxy-1-methyl-ethylamino, 2-methoxy-2-methyl-ethylamino, 1,1-dimethyl-2-methoxy-ethylamino, 1,1-dimethyl-3-methoxy-n-propyl-amino, 3-methoxy-propylamino or 3-[N-(ethoxycarbonyl)-amino]-n-propylamino; or $R_1$ is an imidazolidin-2-ylidene, tetrahydropyrimidin-2-ylidene or hexahydro-1,3-diazepin-2-ylidene moiety which is optionally substituted, especially unsubstituted or substituted by one to three lower alkyl moieties, especially methyl, ethyl, propyl or isopropyl, which may be bound to carbon or nitrogen ring atoms; or $R_1$ is N-oxazolidin-2-one, N-oxazolidin-2-thione, N-[1,2,3] oxathiazolidine-2-oxide, N-[1,2,3]oxathiazolidine-2,2-dioxide, N-pyrrolidin-2-one, N-pyrrolidin-2-thione, N-pyrrolidine-2,5-dione, N-thiazolidin-2-one, N-4-methyleneoxazolidin-2-one, N-piperidine-2,6-dione, N-morpholine-2,3-dione,
N-morpholine-2,5-dione, N-imidazolidin-2-one, N-[1,2,4]-oxazolidin-5-one, N-[1,2,4]-oxazolidin-3-one, N-[1,2,5] oxadiazinan-6-one, N-[1,2,4]oxadiazinan-3-one, azepan-2-one or [1,3]oxazinan-2-one; or $R_1$ is N-oxazolidin-2-one, N-oxazolidin-2-thione, N-[1,2,3] oxathiazolidine-2-oxide and N-pyrrolidin-2-one;

$R_2$ is hydrogen, $C_3$-$C_4$-alkenyl, $C_3$-$C_4$-alkynyl, —$CH_2OR_{16}$, $CH_2SR_{16}$, —C(O)$R_{16}$, —C(O)O$R_{16}$, SO$R_{16}$ or S$R_{16}$; or $R_2$ is hydrogen, —$CH_2OR_{16}$, $CH_2SR_{16}$ or S$R_{16}$; where $R_{16}$ is as defined above;

$R_3$ is H, OH, halogen, loweralkyl, lower alkoxy, CN or
$R_3$ is H, Cl, F, OH, $CH_3$ or $OCH_3$ or
$R_3$ is H or F or
$R_3$ is H;

$R_4$ is hydrogen, halogen, optionally substituted alkyl, optionally substituted alkenyl, optionally substituted alkinyl, optionally substituted alkoxy, optionally substituted alkenyloxy, optionally substituted alkynyloxy, optionally substituted thioalkyl optionally substituted aryl, COOR$_{17}$, CONR$_{18}$R$_{19}$, S(O)$_k$R$_{20}$, SO$_2$NR$_{21}$R$_{22}$ or NR$_{23}$R$_{24}$ where $R_{17}$, $R_{18}$, $R_{19}$, $R_{20}$, $R_{21}$, $R_{22}$, $R_{23}$ and $R_{24}$ are H or $C_{1-4}$ alkyl; or $R_4$ is hydrogen, $C_1$-$C_6$alkyl, $C_1$-$C_6$haloalkyl, $C_1$-$C_6$cyanoalkyl, $C_3$-$C_7$cycloalkyl, $C_2$-$C_6$alkenyl, $C_2$-$C_6$haloalkenyl, $C_2$-$C_6$alkynyl, $C_2$-$C_6$haloalkynyl, amino, $C_1$-$C_6$alkylamino, di($C_1$-$C_6$alkyl)-amino, halogen, hydroxy, mercapto, cyano, $C_1$-$C_6$alkoxy, $C_3$-$C_6$alkenyloxy, $C_3$-$C_6$alkynyloxy, $C_1$-$C_6$haloalkoxy, $C_1$-$C_8$alkanoyloxy-$C_1$-$C_6$alkyl, $C_1$-$C_6$alkylthio, $C_1$-$C_6$alkylsulfinyl, $C_1$-$C_6$alkylsulfonyl, $C_1$-$C_6$hydroxyalkyl, ($C_1$-$C_4$alkoxy)$_n$-$C_1$-$C_4$alkyl, $C_1$-$C_6$aminoalkyl, $C_1$-$C_4$alkyl-$C_1$-$C_6$aminoalkyl, di($C_1$-

$C_4$alkyl)-$C_1$-$C_6$aminoalkyl, $C_1$-$C_8$alkoxycarbonyl, $C_1$-$C_8$alkanoyl-$C_1$-$C_6$aminoalkyl, optionally substituted heterocyclyl, optionally substituted aryl, optionally substituted heteroaryl, or a group —CO—$R_{39}$, —O—CO—$R_9$, —NH—CO—$R_{39}$, —($C_1$-$C_6$alkylene-)-CO—$R_{39}$, —$C_1$-$C_4$(—O—$C_1$-$C_6$alkylene-O—)$_n$—$R_{39}$, —C(=NO $R_{39}$)—$R_{40}$ or —CO—N $R_{39}R_{40}$; where $R_{39}$, $R_{40}$, are independently H or optionally substituted alkyl;

$R_5$ is hydrogen, halogen, optionally substituted alkyl, optionally substituted alkenyl, optionally substituted alkinyl, optionally substituted alkoxy, optionally substituted alkenyloxy, optionally substituted alkynyloxy, optionally substituted thioalkyl optionally substituted aryl, COO$R_{41}$, CON$R_{42}R_{43}$, S(O)$_q R_{44}$, SO$_2 N_{45}R_{46}$ or N$R_{45a}R_{46a}$ where $R_{41}$, $R_{42}$, $R_{43}$, $R_{44}$, $R_{45}$, $R_{46}$ $R_{45a}$, $R_{46a}$, are independently H or optionally substituted alkyl or $R_5$ is hydrogen, $C_1$-$C_6$alkyl, $C_1$-$C_6$haloalkyl, $C_1$-$C_6$cyanoalkyl, $C_3$-$C_7$cycloalkyl, $C_2$-$C_6$alkenyl, $C_2$-$C_6$haloalkenyl, $C_2$-$C_6$alkynyl, $C_2$-$C_6$haloalkynyl, amino, $C_1$-$C_6$alkylamino, di($C_1$-$C_6$alkyl)-amino, halogen, hydroxy, mercapto, cyano, $C_1$-$C_6$alkoxy, $C_3$-$C_6$alkenyloxy, $C_3$-$C_6$alkynyloxy, $C_1$-$C_6$haloalkoxy, $C_1$-$C_8$alkanoyloxy-$C_1$-$C_6$alkyl, $C_1$-$C_6$alkylthio, $C_1$-$C_6$alkylsulfinyl, $C_1$-$C_6$alkylsulfonyl, $C_1$-$C_6$hydroxyalkyl, ($C_1$-$C_4$alkoxy)$_n$-$C_1$-$C_6$alkyl, $C_1$-$C_6$aminoalkyl, $C_1$-$C_4$alkyl-$C_1$-$C_6$aminoalkyl, di($C_1$-$C_4$alkyl)-$C_1$-$C_6$aminoalkyl, $C_1$-$C_8$alkoxycarbonyl, $C_1$-$C_8$alkanoyl-$C_1$-$C_6$aminoalkyl, optionally substituted heterocyclyl, optionally substituted aryl, optionally substituted heteroaryl, or a group —CO—$R_{52}$, —O—CO—$R_{52}$, —NH—CO—$R_{52}$, —($C_1$-$C_6$alkylene-)-CO—$R_{52}$, —$C_1$-$C_4$(—O—$C_1$-$C_6$alkylene-O—)$_n$—$R_{47}$, —C(=NO$R_{48}$)—$R_{49}$ or —CO—N$R_{50}R_{51}$ where $R_{47}$ $R_{48}$, $R_{49}$, $R_{50}$, $R_{51}$ and $R_{52}$ are independently H or optionally substituted alkyl;

$R_6$ is hydrogen, $C_1$-$C_6$alkyl or $C_1$-$C_6$haloalkyl; halogen, hydroxy, mercapto, cyano, $C_1$-$C_6$alkoxy, $C_1$-$C_6$alkylthio, amino, $C_1$-$C_6$alkylamino, di($C_1$-$C_6$alkyl)-amino, —O—CO—$R_{54}$, —NH—CO—$R_{53}$, where $R_{53}$ and $R_{54}$, are independently H or optionally substituted alkyl.

Preferred individual compounds of the formula I are listed in the following Tables:

TABLE A1(a)

Compounds of formula I in which A and A' have the same value designated in the Table as "A" and j, $R_1$, $R_2$, $R_3$, $R_4$, $R_5$ and $R_6$ have the values shown.

| No. | A | R1 | R2 | R3 | R4 | R5 | R6 | j | mp/° C. |
|---|---|---|---|---|---|---|---|---|---|
| A1.01 | N | NHCH(CH$_3$)CH$_2$OCH$_3$ | H | H | H | CF3 | H | 0 | 193-194 |
| A1.02 | N | NHCH(CH$_3$)CH$_2$OCH$_3$ | H | H | H | H | H | 0 | 147-148 |
| A1.03 | N | NHCH(CH$_3$)CH$_2$OCH$_3$ | H | H | Cl | H | H | 0 | 158-159 |
| A1.04 | N | NHCH(CH$_3$)CH$_2$OCH$_3$ | H | H | H | Cl | H | 0 | 200-201 |
| A1.05 | N | NHCH(CH$_3$)CH$_2$OCH$_3$ | H | H | CH$_3$ | H | H | 0 | 168-169 |
| A1.06 | N | NHCH(CH$_3$)CH$_2$OCH$_3$ | H | H | H | CH$_3$ | H | 0 | 185-187 |
| A1.07 | N | NHCH(CH$_3$)CH$_2$OCH$_3$ | H | H | CF3 | H | H | 0 | 192-193 |
| A1.08 | N | NHCH(CH$_3$)CH$_2$OCH$_3$ | H | H | OCH$_3$ | H | H | 0 | 124-125 |
| A1.09 | N | NHCH(CH$_3$)CH$_2$OCH$_3$ | H | H | H | OCH$_3$ | H | 0 | 159-160 |
| A1.10 | CH | NHCH(CH$_3$)CH$_2$OCH$_3$ | H | H | Cl | H | H | 0 | 110 |
| A1.11 | CH | 4-methyl-oxazolidin-2-one | H | H | Cl | H | H | 0 | 220-221 |

TABLE A1(b)

Compounds of formula I in which A is CH and A' is N and j, $R_1$, $R_2$, $R_3$, $R_4$, $R_5$ and $R_6$ have the values shown. For these compounds either mp are given or retention times (RT) (using a YMC CombiScreen ODS-AQ column; 30 x 4.6 mm; 5 um; solvent mixture: 89% H2O + 11% CH$_3$CN (0.1TFA) at a flow rate of 3.5 ml/min).

| No. | R1 | R2 | R3 | R4 | R5 | R6 | j | mp/° C. RT |
|---|---|---|---|---|---|---|---|---|
| A1.12 | 4-methyl-oxazolidin-2-one | H | H | Cl | OH | H | 0 | 178-80 |
| A1.13 | 4-methyl-oxazolidin-2-one | H | OH | Cl | H | H | 0 | 225-226 |
| A1.14 | 4-methyl-oxazolidin-2-one | H | OH | H | H | Cl | 0 | 213-215 |
| A1.15 | NHCH(CH3)CH2OCH3 | H | H | H | OMe | Cl | 0 | 108-110 |
| A1.16 | NHCH(CH3)CH2OCH3 | H | H | H | Me | Cl | 0 | 145-146 |
| A1.17 | NHCH(CH3)CH2OCH3 | H | H | Cl | H | Cl | 0 | 147-148 |
| A1.18 | NHCH(CH3)CH2OCH3 | H | H | H | F | Cl | 0 | 139-141 |
| A1.19 | NHCH(CH3)CH2OCH3 | H | H | F | H | F | 0 | 142-144 |
| A1.20 | NHCH(CH3)CH2OCH3 | H | H | H | H | NO$_2$ | 0 | 113-114 |
| A1.21 | NHCH(CH$_3$)CH$_2$OCH$_3$ | H | H | H | CO$_2$Me | H | 0 | 159-161 |
| A1.22 | NHCH(CH$_3$)CH$_2$OCH$_3$ | H | H | H | —NH—CH=CH— | | 0 | 82-85 |
| A1.23 | NHCH(CH$_3$)CH$_2$OCH$_3$ | H | H | H | —NH—N=CH— | | 0 | 165-169 |
| A1.24 | NHCH(CH$_3$)CH$_2$OCH$_3$ | H | H | H | —O—CF$_2$—O— | | 0 | 140-144 |
| A1.25 | NHCH(CH$_3$)CH$_2$OCH$_3$ | H | H | H | —CH=N—NH— | | 0 | 187-188 |
| A1.26 | —N(morpholino) | H | H | H | —O—CF$_2$—O— | | 0 | 199-200 |
| A1.27 | NHCH(CH$_3$)CH$_2$OH | H | F | Cl | H | H | 0 | 140-141 |
| A1.28 | NHCHCH$_2$OH | H | F | H | H | Cl | 0 | 156-157 |
| A1.29 | NHCH(CH$_3$)CH$_2$OCH$_3$ | H | H | H | H | SMe | 0 | 120-122 |

TABLE A1(b)-continued

Compounds of formula I in which A is CH and A' is N and j, $R_1$, $R_2$, $R_3$, $R_4$, $R_5$ and $R_6$ have the values shown. For these compounds either mp are given or retention times (RT) (using a YMC CombiScreen ODS-AQ column; 30 x 4.6 mm; 5 um; solvent mixture: 89% H2O + 11% CH3CN (0.1TFA) at a flow rate of 3.5 ml/min).

| No. | R1 | R2 | R3 | R4 | R5 | R6 | j | mp/° C. RT |
|---|---|---|---|---|---|---|---|---|
| A1.30 | NHCH(CH₃)CH₂OCH₃ | H | H | H | H | SCF₃ | 0 | 133-134 |
| A1.31 | NHCH(CH₃)CH₂OH | H | Me | Cl | H | H | 0 | 150 |
| A1.32 | NHCH(CH₃)CH₂OCH₃ | H | H | H | —CH=CH—S(O2)— | | 0 | resin |
| A1.33 | NHCH(CH₃)CH₂OCH₃ | H | H | H | —NH—C(Me)=CH— | | 0 | 98-101 |
| A1.34 | NHCH(CH₃)CH₂OAc | H | H | H | H | —NHAc | 0 | 163 |
| A1.35 | NHCH₂CH₂CH₂OH | H | H | H | —O—CF₂—O— | | 0 | 189-192 |
| A1.36 | NHCH(CH₃)CH₂OCH₃ | H | F | H | H | SO₂Me | 0 | resin |
| A1.37 | NHCH(CH₃)CH₂OCH₃ | H | H | H | H | SO₂Me | 0 | resin |
| A1.38 | NHCH₂CH₂CH₂OH | H | H | H | Cl | Cl | 0 | solid |
| A1.39 | NHCH₂CH₂CH₂OH | H | H | H | Cl | H | 0 | 192-194 |
| A1.40 | NHCH₂CH₂CH₂OH | H | Cl | H | Cl | H | 0 | 139-142 |
| A1.41 | NHCH₂CH₂CH₂OH | H | H | Cl | H | Cl | 0 | 141-144 |
| A1.42 | NHCH₂CH₂CH₂OH | H | F | H | H | H | 0 | 123-126 |
| A1.43 | NHCH₂CH₂CH₂OH | H | H | H | CH₃ | H | 0 | 185-187 |
| A1.44 | NHCH₂CH₂CH₂OH | H | H | H | H | SMe | 0 | 98-100 |
| A1.45 | NHCH₂CH₂CH₂OH | H | H | NO₂ | H | H | 0 | 152-155 |
| A1.46 | NHC₆H₃—2F,5Cl | H | F | H | H | Cl | 0 | 234-235 |
| A1.47 | NH₂ | H | H | H | F | Cl | 0 | solid |
| A1.48 | NHCH₂CH₂NHAc | H | H | H | F | Cl | 0 | solid |
| A1.49 | NHCH₂CH₂CH₂OH | H | H | H | OH | H | 0 | solid |
| A1.50 | NHCH₂CH₂C(=O)NH₂ | H | H | H | F | Cl | 0 | solid |
| A1.51 | NHCH₂CH₂C(CH₃)₂OH | H | H | H | F | Cl | 0 | solid |
| A1.52 | NHCH₂CH₂CH₂NH₂ | H | H | H | F | Cl | 0 | solid |
| A1.53 | NHCH₂CH₂C(=O)OH | H | H | H | F | Cl | 0 | solid |
| A1.54 | NHCH₂CH₂CH₂OH | H | F | H | F | H | 0 | 148-151 |
| A1.55 | NHCH₂CH₂CH₂OH | H | Me | H | H | H | 0 | 106-109 |
| A1.56 | NHCH₂CH₂CH₂OH | H | Cl | H | H | H | 0 | 86-89 |
| A1.57 | NHCH₂CH₂CH₂OH | H | H | H | OMe | H | 0 | 142-145 |
| A1.58 | NHCH₂CH₂CH₂OH | H | H | H | F | H | 0 | 190-193 |
| A1.59 | NHCH₂CH₂CH₂OH | H | H | H | F | F | 0 | 181-184 |
| A1.60 | NHCH(CH₃)CH₂OCH₃ | H | H | H | CO₂Me | H | 0 | 1.07 min |
| A1.61 | NHCH(CH₃)CH₂OCH₃ | H | H | H | i-Prop | H | 0 | 1.5 min |
| A1.62 | NHCH(CH₃)CH₂OCH₃ | H | H | H | OEt | H | 0 | 1.11 min |
| A1.63 | NHCH(CH₃)CH₂OCH₃ | H | H | H | F | NO₂ | 0 | 1.15 min |
| A1.64 | NHCH(CH₃)CH₂OCH₃ | H | H | Cl | H | Cl | 0 | 1.61 min |
| A1.65 | NHCH(CH₃)CH₂OCH₃ | H | H | CF₃ | H | CF₃ | 0 | 1.76 min |
| A1.66 | NHCH(CH₃)CH₂OCH₃ | H | H | H | Me | H | 0 | 1.17 min |
| A1.67 | NHCH(CH₃)CH₂OCH₃ | H | H | H | H | NH₂ | 0 | 0.26 min |
| A1.68 | NHCH(CH₃)CH₂OCH₃ | H | H | H | OMe | H | 0 | 0.9 min |
| A1.69 | NHCH(CH₃)CH₂OCH₃ | H | H | H | Br | H | 0 | 1.69 min |
| A1.70 | NHCH(CH₃)CH₂OCH₃ | H | H | H | NO₂ | H | 0 | 1.15 min |
| A1.71 | NHCH(CH₃)CH₂OCH₃ | H | H | H | Et | H | 0 | 1.3 min |
| A1.72 | NHCH(CH₃)CH₂OCH₃ | H | H | H | CN | H | 0 | 1.0 min |
| A1.73 | NHCH(CH₃)CH₂OCH₃ | H | H | Cl | OH | Cl | 0 | 1.02 min |
| A1.74 | NHCH(CH₃)CH₂OCH₃ | H | H | H | NH₂ | H | 0 | 0.26 min |
| A1.75 | NHCH(CH₃)CH₂OCH₃ | H | H | Cl | Me | H | 0 | 1.46 min |
| A1.76 | NHCH(CH₃)CH₂OCH₃ | H | H | H | Cl | Cl | 0 | 1.54 min |
| A1.77 | NHCH(CH₃)CH₂OCH₃ | H | H | H | Me | NO₂ | 0 | 1.26 min |
| A1.78 | NHCH(CH₃)CH₂OCH₃ | H | H | H | OMe | Cl | 0 | 1.2 min |
| A1.79 | NHCH(CH₃)CH₂OCH₃ | H | H | H | F | Cl | 0 | 1.35 min |
| A1.80 | NHCH(CH₃)CH₂OCH₃ | H | H | H | t-Bu | H | 0 | 1.65 min |
| A1.81 | NHCH(CH₃)CH₂OCH₃ | H | H | F | H | F | 0 | 1.3 min |
| A1.82 | NHCH(CH₃)CH₂OCH₃ | H | H | H | C(O)Et | H | 0 | 1.11 min |
| A1.83 | NHCH(CH₃)CH₂OCH₃ | H | H | H | N(Me)Ac | H | 0 | 0.7 min |
| A1.84 | NHCH(CH₃)CH₂OCH₃ | H | H | OMe | H | OMe | 0 | 1.11 min |
| A1.85 | NHCH(CH₃)CH₂OCH₃ | H | H | H | H | NO₂ | 0 | 1.11 min |
| A1.86 | NHCH(CH₃)CH₂OCH₃ | H | H | H | SCN | H | 0 | 1.2 min |
| A1.87 | NHCH(CH₃)CH₂OCH₃ | H | H | H | OMe | OMe | 0 | 0.8 min |
| A1.88 | NHCH(CH₃)CH₂OCH₃ | H | H | F | Br | CF₃ | 0 | 1.63 min |
| A1.89 | NHCH(CH₃)CH₂OCH₃ | H | H | Br | OH | Br | 0 | 1.11 min |
| A1.90 | NHCH(CH₃)CH₂OCH₃ | H | H | H | H | OH | 0 | 0.65 min |
| A1.91 | NHCH(CH₃)CH₂OCH₃ | H | H | H | O—CH₂—O—CH₂ | | 0 | 0.9 min |
| A1.92 | NHCH(CH₃)CH₂OCH₃ | H | H | H | Cl | CF₃ | 0 | 1.61 min |
| A1.93 | NHCH(CH₃)CH₂OCH₃ | H | H | H | OMe | CF₃ | 0 | 1.33 min |
| A1.94 | NHCH(CH₃)CH₂OCH₃ | H | H | H | OH | OMe | 0 | 0.6 min |
| A1.95 | NHCH(CH₃)CH₂OCH₃ | H | H | H | Cl | SH | 0 | 0.8 min |
| A1.96 | NHCH(CH₃)CH₂OCH₃ | H | H | H | Cl | OH | 0 | 0.96 min |
| A1.97 | NHCH(CH₃)CH₂OCH₃ | H | H | H | C(O)N(Me)OMe | Cl | 0 | 0.9 min |
| A1.98 | NHCH(CH₃)CH₂OCH₃ | H | H | H | Me | F | 0 | 1.3 min |
| A1.99 | NHCH(CH₃)CH₂OCH₃ | H | H | H | Br | Cl | 0 | 1.56 min |
| A1.100 | NHCH(CH₃)CH₂OCH₃ | H | H | H | SCF₃ | Cl | 0 | 1.82 min |
| A1.101 | NHCH(CH₃)CH₂OCH₃ | H | H | H | C(Me)₂C(Me)₂NO₂ | H | 0 | 1.54 min |

TABLE A1(b)-continued

Compounds of formula I in which A is CH and A' is N and j, $R_1$, $R_2$, $R_3$, $R_4$, $R_5$ and $R_6$ have the values shown. For these compounds either mp are given or retention times (RT) (using a YMC CombiScreen ODS-AQ column; 30 x 4.6 mm; 5 um; solvent mixture: 89% H2O + 11% $CH_3CN$ (0.1TFA) at a flow rate of 3.5 ml/min).

| No. | R1 | R2 | R3 | R4 | R5 | R6 | j | mp/° C. RT |
|---|---|---|---|---|---|---|---|---|
| A1.102 | $NHCH(CH_3)CH_2OCH_3$ | H | H | H | $SCF_3$ | H | 0 | 1.65 min |
| A1.103 | $NHCH(CH_3)CH_2OCH_3$ | H | H | H | OMe | F | 0 | 1.04 min |
| A1.104 | $NHCH(CH_3)CH_2OCH_3$ | H | H | OMe | H | $CF_3$ | 0 | 1.48 min |
| A1.105 | $NHCH(CH_3)CH_2OCH_3$ | H | H | H | H | $C(O)N(Et)_2$ | 0 | 0.96 min |
| A1.106 | $NHCH(CH_3)CH_2OCH_3$ | H | H | H | F | $CF_3$ | 0 | 1.43 min |
| A1.107 | $NHCH(CH_3)CH_2OCH_3$ | H | H | H | $SO_2N$-iProp | H | 0 | 1.0 min |
| A1.108 | $NHCH(CH_3)CH_2OCH_3$ | H | H | H | $SO_2NEt$ | H | 0 | 0.9 min |
| A1.109 | $NHCH(CH_3)CH_2OCH_3$ | H | H | H | $CO_2Me$ | Br | 0 | 1.26 min |
| A1.110 | $NHCH(CH_3)CH_2OCH_3$ | H | H | H | Cl | $CO_2Me$ | 0 | 1.26 min |
| A1.111 | $NHCH(CH_3)CH_2OCH_3$ | H | H | H | —O—$CH_2$—O— | | 0 | 1.0 min |
| A1.112 | $NHCH(CH_3)CH_2OCH_3$ | H | H | H | H | $CH_2CO_2H$ | 0 | 0.7 min |
| A1.113 | $NHCH(CH_3)CH_2OCH_3$ | H | H | H | =N—S—N= | | 0 | 1.02 min |
| A1.114 | $NHCH(CH_3)CH_2OCH_3$ | H | H | H | H | $SO_2CF_3$ | 0 | 1.41 min |
| A1.115 | $NHCH(CH_3)CH_2OCH_3$ | H | H | H | F | H | 0 | 151-152 |
| A1.116 | $NHCH(CH_3)CH_2OCH_3$ | H | H | H | —C(O)—N(Me)—C(O)— | | 0 | 204-205 |
| A1.117 | $NHCH(CH_3)CH_2OCH_3$ | H | H | H | $CH_2CN$ | H | 0 | 139-140 |
| A1.118 | $NHCH(CH_3)CH_2OCH_3$ | H | H | H | —O—C(O)—CH=CH— | | 0 | 170-172 |
| A1.119 | $NHCH(CH_3)CH_2OCH_3$ | H | H | H | —N(Ac)—$CH_2$—$CH_2$— | | 0 | 0.6 min |
| A1.120 | $NHCH(CH_3)CH_2OCH_3$ | H | H | H | CN | CN | 0 | 1.1 min |
| A1.121 | $NHCH(CH_3)CH_2OCH_3$ | H | H | H | $N(Et)_2$ | H | 0 | 0.5 min |
| A1.122 | $NHCH(CH_3)CH_2OCH_3$ | H | H | H | $NO_2$ | $CF_3$ | 0 | 1.46 min |
| A1.123 | $NHCH(CH_3)CH_2OCH_3$ | H | H | H | CN | Cl | 0 | 1.26 min |
| A1.124 | $NHCH(CH_3)CH_2OCH_3$ | H | H | H | $CO_2H$ | H | 0 | 0.65 min |
| A1.125 | $NHCH(CH_3)CH_2OCH_3$ | H | H | H | OMe | OH | 0 | 0.7 min |
| A1.126 | $NHCH(CH_3)CH_2OCH_3$ | H | H | H | —S—C(O)—N— | | 0 | 0.9 min |
| A1.127 | $NHCH(CH_3)CH_2OCH_3$ | H | H | H | $SO_2CF_3$ | H | 0 | 1.48 min |
| A1.128 | $NHCH(CH_3)CH_2OCH_3$ | H | H | H | H | CN | 0 | 120-122 |
| A1.129 | $NHCH(CH_3)CH_2OCH_3$ | H | H | H | $CH_2$—$CH_2$—$CH_2$— | | 0 | 137-39 |
| A1.130 | $NHCH(CH_3)CH_2OCH_3$ | H | H | $CH_3$ | H | $CH_3$ | 0 | 123-26 |
| A1.131 | $NHCH(CH_3)CH_2OCH_3$ | H | H | H | CH₃C(O)NH-CH₂CH₂-N(morpholino) | H | 0 | 125-29 |
| A1.132 | $NHCH(CH_3)CH_2OCH_3$ | H | H | H | CH₃C(O)NH-CH₂CH₂-N(piperidino) | H | 0 | 74-138 |
| A1.133 | $NHCH(CH_3)CH_2OCH_3$ | H | H | H | 4-acetyl-1-piperazinyl-CH₂-C(O)-N(pyrrolidino) | H | 0 | 103-16 |
| A1.134 | $NHCH(CH_3)CH_2OCH_3$ | H | H | H | 1-acetyl-4-methyl-piperazinyl | H | 0 | 97-101 |
| A1.135 | $NHCH(CH_3)CH_2OCH_3$ | H | H | H | 1-acetyl-4-hydroxy-piperidinyl | H | 0 | 129-31 |

TABLE A1(b)-continued

Compounds of formula I in which A is CH and A' is N and j, $R_1$, $R_2$, $R_3$, $R_4$, $R_5$ and $R_6$ have the values shown. For these compounds either mp are given or retention times (RT) (using a YMC CombiScreen ODS-AQ column; 30 x 4.6 mm; 5 um; solvent mixture: 89% H2O + 11% CH$_3$CN (0.1TFA) at a flow rate of 3.5 ml/min).

| No. | R1 | R2 | R3 | R4 | R5 | R6 | j | mp/° C. RT |
|---|---|---|---|---|---|---|---|---|
| A1.136 | NHCH(CH$_3$)CH$_2$OCH$_3$ | H | H | H | (acetamido-propyl-pyrrolidinone) | H | 0 | amorphous |
| A1.137 | NHCH(CH$_3$)CH$_2$OCH$_3$ | H | H | H | ((1-methylpiperidin-3-yl)methyl acetate) | H | 0 | amorphous |
| A1.138 | NHCH(CH$_3$)CH$_2$OCH$_3$ | H | H | H | (N-(2-pyrrolidin-1-yl-ethyl)acetamide) MeSO$_3$H | H | 0 | amorphous |
| A1.139 | NHCH(CH$_3$)CH$_2$OCH$_3$ | H | H | H | (N-(2-(1-methylpyrrolidin-2-yl)ethyl)acetamide) MeSO$_3$H | H | 0 | amorphous |
| A1.140 | NHCH(CH$_3$)CH$_2$OCH$_3$ | H | H | H | (1-acetyl-4-(2-oxo-2-pyrrolidin-1-yl-ethyl)piperazine) MeSO$_3$H | H | 0 | amorphous |

TABLE A1(b)-continued

Compounds of formula I in which A is CH and A' is N and j, $R_1$, $R_2$, $R_3$, $R_4$, $R_5$ and $R_6$ have the values shown. For these compounds either mp are given or retention times (RT) (using a YMC CombiScreen ODS-AQ column; 30 x 4.6 mm; 5 um; solvent mixture: 89% H2O + 11% $CH_3CN$ (0.1TFA) at a flow rate of 3.5 ml/min).

| No. | R1 | R2 | R3 | R4 | R5 | R6 | j | mp/° C. RT |
|---|---|---|---|---|---|---|---|---|
| A1.141 | $NHCH(CH_3)CH_2OCH_3$ | H | H | H | (N-methyl sulfonamide, p-tolyl) | H | 0 | amorphous |
| A1.142 | $NHCH(CH_3)CH_2OCH_3$ | H | H | H | (N-methyl methanesulfonamide, Me⁻) | H | 0 | amorphous |
| A1.143 | $NHCH(CH_3)CH_2OCH_3$ | H | H | H | (N-methyl sulfonamide-phenyl-NHC(O)CH_3) | OMe | 0 | amorphous |
| A1.144 | $NHCH(CH_3)CH_2OCH_3$ | H | H | H | H | (acetamido-ethyl-morpholine) | 0 | 145-47 |
| A1.145 | $NHCH(CH_3)CH_2OCH_3$ | H | H | H | H | (acetyl-piperazine-CH_2-C(O)-pyrrolidine) | 0 | 86-90 |
| A1.146 | $NHCH(CH_3)CH_2OCH_3$ | H | H | H | H | (acetamido-ethyl-morpholine, $MeSO_3H$) | 0 | 114-18 |

TABLE A1(b)-continued

Compounds of formula I in which A is CH and A' is N and j, $R_1$, $R_2$, $R_3$, $R_4$, $R_5$ and $R_6$ have the values shown. For these compounds either mp are given or retention times (RT) (using a YMC CombiScreen ODS-AQ column; 30 x 4.6 mm; 5 um; solvent mixture: 89% H2O + 11% CH$_3$CN (0.1TFA) at a flow rate of 3.5 ml/min).

| No. | R1 | R2 | R3 | R4 | R5 | R6 | j | mp/° C. RT |
|---|---|---|---|---|---|---|---|---|
| A1.147 | NHCH(CH$_3$)CH$_2$OCH$_3$ | H | H | H | H | 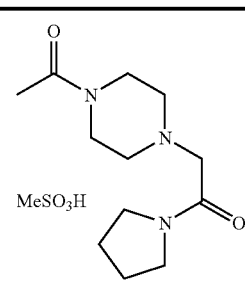 MeSO$_3$H | 0 | 154-59 |
| A1.148 | NHCH(CH$_3$)CH$_2$OCH$_3$ | H | H | H | H | —CO$_2$H | 0 | 91-92 |
| A1.149 | NHCH(CH$_3$)CH$_2$OCH$_3$ | H | H | H | 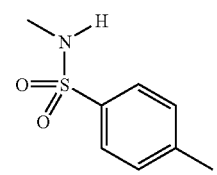 | Me | 0 | amorphous |
| A1.150 | NHCH(CH$_3$)CH$_2$OCH$_3$ | H | H | H | H | 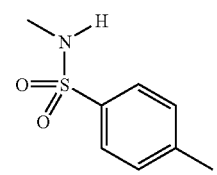 | 0 | amorphous |
| A1.151 | NHCH(CH$_3$)CH$_2$OCH$_3$ | H | H | H | —SF$_5$ | H | 0 | 198-200 |
| A1.152 | NHCH(CH$_3$)CH$_2$OCH$_3$ | H | H | H | H | —SF$_5$ | 0 | 121-24 |
| A1.153 | NHCH(CH$_3$)CH$_2$OCH$_3$ | H | H | H | Cl | H | 0 | 150-53 |
| A1.154 | NHCH(CH$_3$)CH$_2$OCH$_3$ | H | F | H | H | NO$_2$ | 0 | 1.23 min |
| A1.155 | NHCH(CH$_3$)CH$_2$OCH$_3$ | H | H | H | OC$_6$H$_4$—4Cl | H | 0 | 1.7 min |
| A1.156 | NHCH(CH$_3$)CH$_2$OCH$_3$ | H | Me | H | H | Me | 0 | 1.28 min |
| A1.157 | NHCH(CH$_3$)CH$_2$OCH$_3$ | H | H | H | Cl | NO$_2$ | 0 | 1.4 min |
| A1.158 | NHCH(CH$_3$)CH$_2$OCH$_3$ | H | H | H | OC$_6$H$_4$—4OMe | H | 0 | 1.5 min |
| A1.159 | NHCH(CH$_3$)CH$_2$OCH$_3$ | H | H | H | —O—CH$_2$—CH$_2$— | | 0 | 1.1 min |
| A1.160 | NHCH(CH$_3$)CH$_2$OCH$_3$ | H | F | H | H | C(O)Me | 0 | 1.15 min |
| A1.161 | NHCH(CH$_3$)CH$_2$OCH$_3$ | H | H | H | —C(O)—CH$_2$—CH$_2$—CH$_2$— | | 0 | 1.19 min |
| A1.162 | NHCH(CH$_3$)CH$_2$OCH$_3$ | H | Me | H | NO2 | OMe | 0 | 1.2 min |
| A1.163 | NHCH(CH$_3$)CH$_2$OCH$_3$ | H | OH | H | H | Me | 0 | 1.0 min |
| A1.164 | NHCH(CH$_3$)CH$_2$OCH$_3$ | H | Cl | H | H | NO$_2$ | 0 | 1.37 min |
| A1.165 | NHCH(CH$_3$)CH$_2$OCH$_3$ | H | H | H | 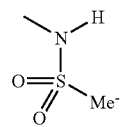 | | 0 | 1.5 min |
| A1.166 | NHCH(CH$_3$)CH$_2$OCH$_3$ | H | H | H | OH | H | 0 | 0.8 min |
| A1.167 | NHCH(CH$_3$)CH$_2$OCH$_3$ | H | H | H | Cl | CO$_2$H | 0 | 0.98 min |
| A1.168 | NHCH(CH$_3$)CH$_2$OCH$_3$ | H | H | H | OPh | H | 0 | 1.5 min |
| A1.169 | NHCH(CH$_3$)CH$_2$OCH$_3$ | H | H | H | OBu(n) | H | 0 | 1.5 min |
| A1.170 | NHCH(CH$_3$)CH$_2$OCH$_3$ | H | Me | H | NO$_2$ | H | 0 | 1.32 min |
| A1.171 | NHCH(CH$_3$)CH$_2$OCH$_3$ | H | H | H | 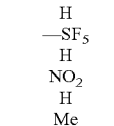 | | 0 | 1.6 min |
| A1.172 | NHCH(CH$_3$)CH$_2$OCH$_3$ | H | OMe | H | Cl | OMe | 0 | 1.4 min |
| A1.173 | NHCH(CH$_3$)CH$_2$OCH$_3$ | H | OMe | H | H | NO$_2$ | 0 | 1.28 min |
| A1.174 | NHCH(CH$_3$)CH$_2$OCH$_3$ | H | OMe | H | H | Me | 0 | 1.36 min |
| A1.175 | NHCH(CH$_3$)CH$_2$OCH$_3$ | H | Br | H | OCF$_3$ | H | 0 | 1.65 min |

TABLE A1(b)-continued

Compounds of formula I in which A is CH and A' is N and j, R₁, R₂, R₃, R₄, R₅ and R₆ have the values shown. For these compounds either mp are given or retention times (RT) (using a YMC CombiScreen ODS-AQ column; 30 x 4.6 mm; 5 um; solvent mixture: 89% H2O + 11% CH₃CN (0.1TFA) at a flow rate of 3.5 ml/min).

| No. | R1 | R2 | R3 | R4 | R5 | R6 | j | mp/° C. RT |
|---|---|---|---|---|---|---|---|---|
| A1.176 | NHCH(CH₃)CH₂OCH₃ | H | H | Me | 3-Cl-5-CF₃-2-oxo-pyridinyl | H | 0 | 1.78 min |
| A1.177 | NHCH(CH₃)CH₂OCH₃ | H | Me | H | 2-cyano-4-CF₃-phenoxy | H | 0 | 1.7 min |
| A1.178 | NHCH(CH₃)CH₂OCH₃ | H | H | H | 3-methyl-1,2,4-thiadiazol-5-yloxy | H | 0 | 1.2 min |
| A1.179 | NHCH(CH₃)CH₂OCH₃ | H | H | H | H | 3,5-dichloro-2-oxo-pyridinyl | 0 | 1.6 min |
| A1.180 | NHCH(CH₃)CH₂OCH₃ | H | F | H | Cl | —C(O)OCH(CH₃)₂ | 0 | 1.57 min |
| A1.181 | NHCH(CH₃)CH₂OCH₃ | H | H | H | 2-(5-methylthiophen-2-yl)ethoxy | Cl | 0 | 1.78 min |
| A1.182 | NHCH(CH₃)CH₂OCH₃ | H | F | H | OH | H | 0 | 0.9 min |
| A1.183 | NHCH(CH₃)CH₂OCH₃ | H | H | H | 2-cyclopropyl-6-CF₃-pyrimidin-4-yloxy | H | 0 | 1.73 min |
| A1.184 | NHCH(CH₃)CH₂OCH₃ | H | F | H | Br | OH | 0 | 1.15 min |
| A1.185 | NHCH(CH₃)CH₂OCH₃ | H | Me | H | OCH(CH₃)CO₂Me | H | 0 | 1.2 min |
| A1.186 | NHCH(CH₃)CH₂OCH₃ | H | H | H | 5-tert-butyl-1,3,4-thiadiazol-2-yloxy | H | 0 | 1.4 min |
| A1.187 | NHCH(CH₃)CH₂OCH₃ | H | H | H | Cl | 2-acetoxy-2-methylpropanoic acid | 0 | 1.32 min |
| A1.188 | NHCH(CH₃)CH₂OCH₃ | H | F | H | Cl | OMe | 0 | 1.32 min |
| A1.189 | NHCH(CH₃)CH₂OCH₃ | H | F | H | Br | CO₂Me | 0 | 1.4 min |

TABLE A1(b)-continued

Compounds of formula I in which A is CH and A' is N and j, $R_1$, $R_2$, $R_3$, $R_4$, $R_5$ and $R_6$ have the values shown. For these compounds either mp are given or retention times (RT) (using a YMC CombiScreen ODS-AQ column; 30 x 4.6 mm; 5 um; solvent mixture: 89% H2O + 11% $CH_3CN$ (0.1TFA) at a flow rate of 3.5 ml/min).

| No. | R1 | R2 | R3 | R4 | R5 | R6 | j | mp/° C. RT |
|---|---|---|---|---|---|---|---|---|
| A1.190 | $NHCH(CH_3)CH_2OCH_3$ | H | OMe | H | NO2 | Cl | 0 | 1.53 min |
| A1.191 | $NHCH(CH_3)CH_2OCH_3$ | H | F | H | Cl | $CH_2CN$ | 0 | 1.32 min |
| A1.192 | $NHCH(CH_3)CH_2OCH_3$ | H | F | H | Cl | $OCH_2CO_2Me$ | 0 | 1.4 min |
| A1.193 | $NHCH(CH_3)CH_2OCH_3$ | H | H | H | O-C6H4-OH (para) | H | 0 | 1.23 min |
| A1.194 | $NHCH(CH_3)CH_2OCH_3$ | H | F | H | H | $CO_2Me$ | 0 | 1.23 min |
| A1.195 | $NHCH(CH_3)CH_2OCH_3$ | H | F | H | Cl | $CO_2H$ | 0 | 1.1 min |
| A1.196 | $NHCH(CH_3)CH_2OCH_3$ | H | F | H | F | $CO_2Me$ | 0 | 1.19 min |
| A1.197 | $NHCH(CH_3)CH_2OCH_3$ | H | Cl | H | H | $CO_2Me$ | 0 | 1.4 min |
| A1.198 | $NHCH(CH_3)CH_2OCH_3$ | H | H | H | $OCF_3$ | H | 0 | 1.4 min |
| A1.199 | $NHCH(CH_3)CH_2OCH_3$ | H | F | H | Cl | Obz | 0 | 1.73 min |
| A1.200 | $NHCH(CH_3)CH_2OCH_3$ | H | F | H | CN | OMe | 0 | 1.3 min |
| A1.201 | $NHCH(CH_3)CH_2OCH_3$ | H | F | H | Br | O-Pent(c) | 0 | 1.8 min |
| A1.202 | $NHCH(CH_3)CH_2OCH_3$ | H | F | H | Br | O-CH2-(2,2-dichloro-3-methylcyclopropyl) | 0 | 1.9 min |
| A1.203 | $NHCH(CH_3)CH_2OCH_3$ | H | F | H | Br | $OCH_2CH(Me)_2$ | 0 | 1.82 min |
| A1.204 | $NHCH(CH_3)CH_2OCH_3$ | H | F | H | Br | OEt | 0 | 1.6 min |
| A1.205 | $NHCH(CH_3)CH_2OCH_3$ | H | F | H | Br | O-CH2-cyclohexyl | 0 | 2.2 min |
| A1.206 | $NHCH(CH_3)CH_2OCH_3$ | H | H | OMe | OMe | OMe | 0 | 1.1 min |
| A1.207 | $NHCH(CH_3)CH_2OCH_3$ | H | Cl | Cl | O-CH2-C≡CH | H | 0 | 1.48 min |
| A1.208 | $NHCH(CH_3)CH_2OCH_3$ | H | Cl | H | H | $NO_2$ | 0 | 1.15 min |
| A1.209 | $NHCH(CH_3)CH_2OCH_3$ | H | Me | H | H | (t)Bu | 0 | 1.61 min |
| A1.210 | $NHCH(CH_3)CH_2OCH_3$ | H | H | H | H | $OCF_2CHFCl$ | 0 | 1.53 min |
| A1.211 | $NHCH(CH_3)CH_2OCH_3$ | H | H | H | 4-bromo-2-ethyl-1-methylphenyl | 0 | 1.82 min |
| A1.212 | $NHCH(CH_3)CH_2OCH_3$ | H | H | H | 2-(2-oxopropyl)phenylthio | 0 | 1.65 min |
| A1.213 | $NHCH(CH_3)CH_2OCH_3$ | H | H | H | Ph | OMe | 0 | 1.61 min |
| A1.214 | $NHCH(CH_3)CH_2OCH_3$ | H | H | H | OBz | H | 0 | 1.57 min |
| A1.215 | $NHCH(CH_3)CH_2OCH_3$ | H | H | H | O-(3-CF3-phenyl) | H | 0 | 1.78 min |

Further compounds of general structure I are those where A and A' are both N and the values of $R_3$ to $R_6$ corresponds with a line of Table B and the values of j, $R_1$ and $R_2$ correspond with a line of Table C.

TABLE B

| No. | R3 | R4 | R5 | R6 |
|---|---|---|---|---|
| B.01 | H | H | H | $CH_3$ |
| B.02 | H | H | H | $C_2H_5$ |
| B.03 | H | H | H | t-Butyl |
| B.04 | H | H | H | iso-Propyl |
| B.05 | H | H | H | OMe |
| B.06 | H | H | H | OEt |
| B.07 | H | H | H | $OCH_2$—C≡CH |
| B.08 | H | H | H | $OCH_2$—CH=$CH_2$ |
| B.09 | H | H | H | $OCF_3$ |
| B.10 | H | H | H | OC(=O)$NMe_2$ |
| B.11 | H | H | H | OH |
| B.12 | H | H | H | $OCF_2CF_3$ |
| B.13 | H | H | H | F |
| B.14 | H | H | H | CL |
| B.15 | H | H | H | BR |
| B.16 | H | H | H | $NO_2$ |
| B.17 | H | H | H | CN |
| B.18 | H | H | H | C(=O)OMe |
| B.19 | H | H | H | C(=O)$OCH_2Ph$ |
| B.20 | H | H | H | C(=O)$C_2H_5$ |
| B.21 | H | H | H | C(=O)$NEt_2$ |
| B.22 | H | H | H | C(=O)$NHCH_2$—C≡CH |
| B.23 | H | H | H | $NHSO_2CH_3$ |
| B.24 | H | H | H | $NHSO_2Ph$ |
| B.25 | H | H | H | NHBu |
| B.26 | H | H | H | $N(Et)_2$ |
| B.27 | H | H | H | NMe-nProp |
| B.28 | H | H | H | $NHCH_2$—C≡CH |
| B.29 | H | H | H | NH–(CH$_2$)$_3$–(1-imidazolyl) |
| B.30 | H | H | H | NH–(CH$_2$)$_3$–(4-methylpiperazin-1-yl) |
| B.31 | H | H | H | NH–(CH$_2$)$_3$–(morpholin-4-yl) |
| B.32 | H | H | H | O–(CH$_2$)$_3$–(1,2,4-triazol-1-yl) |
| B.33 | H | H | H | O–CH$_2$–(pyridin-3-yl) |
| B.34 | H | H | H | C(H)=NOBu |
| B.35 | H | H | H | $O(CH_2)_2O(CH_2)_2OH$ |
| B.36 | H | H | H | SH |
| B.37 | H | H | H | SBu |
| B.38 | H | H | H | SMe |
| B.39 | H | H | H | S–(CH$_2$)$_4$–(piperazin-1-yl)-NH |
| B.40 | H | H | H | $(CH_2)_2C$(=O)NHEt |
| B.41 | H | H | H | $SO_2NHMe$ |
| B.42 | H | H | H | $SO_2NMeEt$ |
| B.43 | H | H | H | $SO_2NH$-iProp |
| B.44 | H | H | H | $SO_2NHEt$ |
| B.45 | H | H | H | $SO_2NHBz$ |
| B.46 | H | H | H | $SO_2CH_3$ |

TABLE B-continued

| No. | R3 | R4 | R5 | R6 |
|---|---|---|---|---|
| B.47 | H | H | H | —CH₂—CH₂—CH₂—N(piperazine)-N-Me |
| B.48 | H | H | H | CH₂—C≡C—Ph |
| B.49 | H | H | H | O—CH₂—C≡C—CH₂—OH |
| B.50 | H | H | H | OH |
| B.51 | H | H | H | CH₂CN |
| B.52 | H | H | H | CH₂OH |
| B.53 | H | H | H | NH₂ |
| B.54 | H | H | H | SO₂CF₃ |
| B.55 | H | H | H | SCF₃ |
| B.56 | H | H | H | C(CH₃)₂OH |
| B.57 | H | H | H | —N(Me)—C(=O)Me |
| B.58 | H | H | H | —NHC(=O)Me |
| B.59 | H | H | H | S(O)Me |
| B.60 | H | H | H | CH₂—CO₂H |
| B.61 | H | H | H | C(=O)Me |
| B.62 | H | H | H | —CO₂H |
| B.63 | H | H | H | —S(=O)₂-piperidine |
| B.64 | H | H | H | —C(=O)NH—CH₂CH₂-(1H-pyrrol-2-yl) |
| B.65 | H | H | H | —C≡C—C(CH₃)₂—OH |
| B.66 | H | H | H | —C(=O)NH—CH₂CH₂CH₂-(1H-imidazol-1-yl) |
| B.67 | H | H | —O—CF₂—O— | |
| B.68 | H | H | —CH=CH—NH— | |
| B.69 | H | H | —CH=CH—C(=O)—O— | |
| B.70 | H | H | —C(=O)—N(Me)—C(=O)— | |
| B.71 | H | H | —CH₂—O—CH₂—O— | |
| B.72 | H | H | —CH=N—NH— | |
| B.73 | H | H | —O—CH₂—O— | |
| B.74 | H | H | —NH—N=CH— | |
| B.75 | H | H | —NH—CH=CH— | |
| B.76 | H | H | =N—S—N= | |
| B.77 | H | H | —CH=CH—SO₂— | |
| B.78 | H | H | —NH—CH=C(Me)— | |
| B.79 | H | H | —N(Ac)—CH₂—CH₂— | |
| B.80 | H | H | —S—C(=O)—NH— | |
| B.81 | H | H | —O—C(=O)—CH=CH— | |
| B.82 | H | H | Cl | Cl |
| B.83 | H | H | Cl | OMe |
| B.84 | H | H | Cl | Me |
| B.85 | H | H | Cl | F |
| B.86 | H | H | Cl | Br |
| B.87 | H | H | Cl | —C(=O)—N(Me)—OMe |
| B.88 | H | H | Cl | OH |
| B.89 | H | H | Cl | SCF₃ |
| B.90 | H | H | Cl | CN |
| B.91 | H | H | CN | CN |
| B.92 | H | H | NO₂ | Me |
| B.93 | H | H | NO₂ | F |
| B.94 | H | H | F | OMe |
| B.95 | H | H | F | Me |
| B.96 | H | H | F | F |
| B.97 | H | H | CF₃ | OMe |
| B.98 | H | H | CF₃ | Br |
| B.99 | H | H | CF₃ | Cl |
| B.100 | H | H | CF₃ | F |
| B.101 | H | H | CF₃ | NO₂ |

TABLE B-continued

| No. | R3 | R4 | R5 | R6 |
|---|---|---|---|---|
| B.102 | H | H | OMe | OMe |
| B.103 | H | H | OMe | OH |
| B.104 | H | H | OH | Cl |
| B.105 | H | H | CO2Me | Cl |
| B.106 | H | H | Br | CO2Me |
| B.107 | H | H | SH | Cl |
| B.108 | H | H | OH | OMe |
| B.109 | H | H | CH₃C(=O)NH(CH₂)₃-imidazol-1-yl | Cl |
| B.110 | H | H | 4-methylpiperazin-1-yl-(CH₂)₃-NH- | Cl |
| B.111 | H | H | C(H)=NOBu | Cl |
| B.112 | H | H | (CH₂)₂C(=O)NHEt | Cl |
| B.113 | H | H | C(CH₃)=NOBu | Cl |
| B.114 | H | H | O(CH₂)₃-(1,2,4-triazol-1-yl) | Cl |
| B.115 | H | H | O(CH₂)₂O(CH₂)₂OH | Cl |
| B.116 | H | H | O-CH₂-(pyridin-3-yl) | Cl |
| B.117 | H | H | Cl | CH₃C(=O)NH(CH₂)₃-imidazol-1-yl |
| B.118 | H | H | Cl | EtNH(CH₂)₃-morpholin-4-yl |
| B.119 | H | H | Cl | O-CH₂-(pyridin-3-yl) |
| B.120 | H | H | CH₃ | H |
| B.121 | H | H | C₂H₅ | H |
| B.122 | H | H | t-Butyl | H |
| B.123 | H | H | iso-Propyl | H |
| B.124 | H | H | OMe | H |
| B.125 | H | H | OEt | H |
| B.126 | H | H | OCH₂—C≡CH | H |
| B.127 | H | H | OCH₂—CH=CH₂ | H |
| B.128 | H | H | OCF₃ | H |
| B.129 | H | H | OC(=O)NMe₂ | H |
| B.130 | H | H | OH | H |
| B.131 | H | H | OCF₂CF₃ | H |
| B.132 | H | H | F | H |
| B.133 | H | H | CL | H |
| B.134 | H | H | BR | H |
| 8.135 | H | H | NO₂ | H |
| B.136 | H | H | CN | H |
| B.137 | H | H | C(=O)OMe | H |
| B.138 | H | H | C(=O)OCH₂Ph | H |
| B.139 | H | H | C(=O)C₂H₅ | H |
| B.140 | H | H | C(=O)NEt₂ | H |
| B.141 | H | H | C(=O)NHCH₂—C≡CH | H |

TABLE B-continued

| No. | R3 | R4 | R5 | R6 |
|---|---|---|---|---|
| B.142 | H | H | NHSO$_2$CH$_3$ | H |
| B.143 | H | H | NHSO$_2$Ph | H |
| B.144 | H | H | NHBu | H |
| B.145 | H | H | N(Et)$_2$ | H |
| B.146 | H | H | NMe-nProp | H |
| B.147 | H | H | NHCH$_2$—C≡CH | H |
| B.148 | H | H | 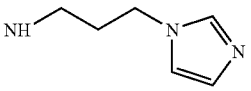 | H |
| B.149 | H | H | 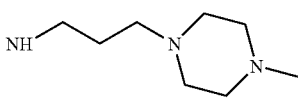 | H |
| B.150 | H | H | 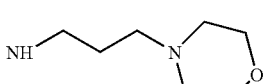 | H |
| B.151 | H | H | 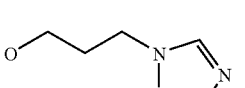 | H |
| B.152 | H | H | 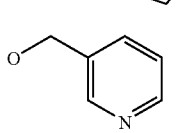 | H |
| B.153 | H | H | C(H)=NOBu | H |
| B.154 | H | H | O(CH$_2$)$_2$O(CH$_2$)$_2$OH | H |
| B.155 | H | H | SH | H |
| B.156 | H | H | SBu | H |
| B.157 | H | H | SMe | H |
| B.158 | H | H | 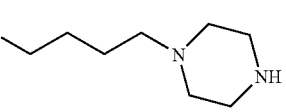 | H |
| B.159 | H | H | (CH$_2$)$_2$C(=O)NHEt | H |
| B.160 | H | H | SO$_2$NHMe | H |
| B.161 | H | H | SO$_2$NMeEt | H |
| B.162 | H | H | SO$_2$NH-iProp | H |
| B.163 | H | H | SO$_2$NHEt | H |
| B.164 | H | H | SO$_2$NHBz | H |
| B.165 | H | H | SO$_2$CH$_3$ | H |
| B.166 | H | H | 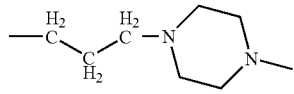 | H |
| B.167 | H | H | CH$_2$—C≡C—Ph | H |
| B.168 | H | H | O—CH$_2$—C≡C—CH$_2$—OH | H |
| B.169 | H | H | OH | H |
| B.170 | H | H | CH$_2$CN | H |
| B.171 | H | H | CH$_2$OH | H |
| B.172 | H | H | NH$_2$ | H |
| B.173 | H | H | SO$_2$CF$_3$ | H |
| B.174 | H | H | SCF$_3$ | H |
| B.175 | H | H | C(CH$_3$)$_2$OH | H |
| B.176 | H | H | —N(Me)—C(=O)Me | H |
| B.177 | H | H | —NHC(=O)Me | H |
| B.178 | H | H | S(O)Me | H |
| B.179 | H | H | CH$_2$—CO$_2$H | H |
| B.180 | H | H | C(=O)Me | H |
| B.181 | H | H | —CO$_2$H | H |

TABLE B-continued

| No. | R3 | R4 | R5 | R6 |
|---|---|---|---|---|
| B.182 | H | H | 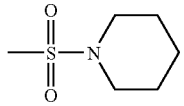 | H |
| B.183 | H | H | 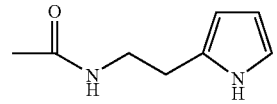 | H |
| B.184 | H | H | —C≡C—C(CH$_3$)$_2$—OH | H |
| B.185 | H | H | 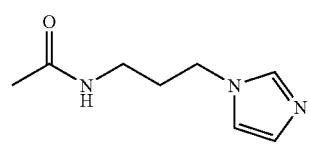 | H |
| B.186 | H | Cl | H | Cl |
| B.187 | H | F | H | F |
| B.188 | H | OMe | H | OMe |
| B.189 | H | CF3 | H | CF3 |
| B.190 | H | Br | OH | Br |
| B.191 | H | Cl | OH | Cl |
| B.192 | F | H | H | H |
| B.193 | Me | H | H | H |
| B.194 | Cl | H | H | H |
| B.195 | OMe | H | H | H |
| B.196 | CN | H | H | H |
| B.197 | F | Cl | H | H |
| B.198 | Me | Cl | H | H |
| B.199 | OH | Cl | H | H |
| B.200 | Cl | H | Cl | H |
| B.201 | F | H | F | H |
| B.202 | F | H | H | Cl |
| B.203 | F | H | H | SO2Me |
| B.204 | OH | H | H | Cl |
| B.205 | OMe | H | H | Cl |
| B.206 | Me | H | H | Cl |

TABLE C

| No. | J | R$_1$ | R$_2$ |
|---|---|---|---|
| C.01 | 0 | N(CH$_3$)N(CH$_2$CF$_3$)$_2$ | H |
| C.02 | 0 | NHNHCH$_2$CH$_2$OCH$_3$ | H |
| C.03 | 0 | N(CH$_2$CH$_2$OCH$_3$)NHC(CH$_3$)$_3$ | H |
| C.04 | 0 | NHN(CH$_3$)CH$_2$OCH$_2$CH$_3$ | H |
| C.05 | 0 | NHNHC(O)CH$_2$CH$_2$OCH$_3$ | H |
| C.06 | 0 | N[C(O)CH$_2$CH$_2$OCH$_3$]NH(CH$_3$) | H |
| C.07 | 0 | N[C(O)CH$_3$]N(CH$_3$)[C(O)CH$_3$] | H |
| C.08 | 0 |  | H |
| C.09 | 0 | 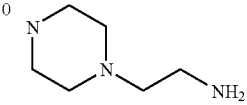 | H |
| C.10 | 0 | NH(CH$_3$) | H |
| C.11 | 0 | N(CH$_3$)$_2$ | H |
| C.12 | 0 | NH[CH(CH$_3$)CH$_2$CH$_3$] | H |
| C.13 | 0 | NHNH$_2$ | H |
| C.14 | 0 | NHNHCH$_3$ | H |

TABLE C-continued

| No. | J | R₁ | R₂ |
|---|---|---|---|
| C.15 | 0 | (2,6-dimethylmorpholin-4-yl) | H |
| C.16 | 0 | NH[CH(CH₃)CH₂CH₂NHCH₃] | H |
| C.17 | 0 | NH[CH(CH₃)CH₂CH₂N(CH₃)₂] | H |
| C.18 | 0 | NH[CH(CH₂CH₃)CH₂N(CH₃)₂] | H |
| C.19 | 0 | NCH₃[(CH₂)₃N(CH₃)₂] | H |
| C.20 | 0 | NCH₃[CH(CH₃)CH₂N(CH₃)₂] | H |
| C.21 | 0 | NH[CH₂CH₂OCH₂OCH₃] | H |
| C.22 | 0 | NH[CH₂CH₂OCH₂OCH₂CH₃] | H |
| C.23 | 0 | NH(CH₂)₂CN | H |
| C.24 | 0 | N(CH₃)(CH₂)₃CN | H |
| C.25 | 0 | NHCH(CH₂CH₃)CH₂CN | H |
| C.26 | 0 | NH(CH₂CH=CH₂) | H |
| C.27 | 0 | NH(CH(CH₃)CH=CH₂) | H |
| C.28 | 0 | NH(CH(CH₃)CH=CH₂) | H |
| C.29 | 0 | NH(CH₂C≡CCH₃) | H |
| C.30 | 0 | NHCH₂CH₂NH—C(O)CH₂CH₃ | H |
| C.31 | 0 | NHCH(CH₃)CH₂NH—C(O)CH₂CH₃ | H |
| C.32 | 0 | NHCH(CH₂CH₃)CH₂CH₂NH—C(O)CH₂OCH₃ | H |
| C.33 | 0 | NHCH(CH₃)CH₂NH—C(O)OCH₂CH₃ | H |
| C.34 | 0 | NHCH(CH₃)COOH | H |
| C.35 | 0 | NHCH₂C(O)N(CH₃)₂ | H |
| C.36 | 0 | NHCH(CH₃)C(O)OCH₂CH(CH₃)OH | H |
| C.37 | 0 | NHCH(CH₃)C(O)NHCH(CH₃)OH | H |
| C.38 | 0 | NHCH₂CH₂CH₂OH | H |
| C.39 | 0 | NHCH₂CH₂CH₂OCH₃ | H |
| C.40 | 0 | NHCH₂CH₂CH₂OCH₂CH₃ | H |
| C.41 | 0 | NHCH[CH(CH₃)₂]OCH₃ | H |
| C.42 | 0 | NHCH(CH(CH₂CH₃)CH₃)—O(CH₂)₂CH₃ | H |
| C.43 | 0 | NHCH(CH₃)CH₂OH | H |
| C.44 | 0 | NHCH(CH₃)CH₂OCH₃ | H |
| C.45 | 0 | NHCH(CH₃)CH₂OCH₂CH₃ | H |
| C.46 | 0 | NHCH(CH₃)CH₂O(CH₂)₂CH₃ | H |
| C.47 | 0 | NHCH(CH₂CH₃)CH₂OCH₃ | H |
| C.48 | 0 | NHCH(CH₂OH)CH₂OH | H |
| C.49 | 0 | NHCH(CH₂OH)CH₂OCH₃ | H |
| C.50 | 0 | NHCH(CH₂OH)CH₂OCH₂CH₃ | H |
| C.51 | 0 | NHCH(CH₂OH)CH₂O(CH₂)₂CH₃ | H |
| C.52 | 0 | NHCH(CH₂OCH₃)CH₂OCH₃ | H |
| C.53 | 0 | NHCH(CH₃)CH₂CH₂OH | H |
| C.54 | 0 | NHCH(CH₃)CH₂CH₂OCH₃ | H |
| C.55 | 0 | NHCH(CH₂OH)CH₂CH₂OCH₃ | H |
| C.56 | 0 | NHCH(CH₂OCH₃)CH₂CH₂OH | H |
| C.57 | 0 | NHCH(CH₃)CH(CH₃)OCH₃ | H |
| C.58 | 0 | NHCH(CH₂CH₃)CH(CH₃)O—CH₂CH₃ | H |
| C.59 | 0 | NHCH(CH₂OH)CH(CH₃)O—(CH₂)₂CH₃ | H |
| C.60 | 0 | N(CH₃)CH₂CH₂OCH₃ | H |
| C.61 | 0 | N(CH₃)CH(CH₂OH)CH₂OH | H |
| C.62 | 0 | N(CH₂OCH₃)CH₂CH₂OCH₃ | H |
| C.63 | 0 | N(CH₂OCH₃)CH(CH₃)CH₂OCH₃ | H |
| C.64 | 0 | N(CH₂OCH₃)CH(CH₂OH)CH₂O—CH₂CH₃ | H |
| C.65 | 0 | N(CH₂OCH₃)CH(CH₃)CH₂CH₂O—(CH₂)₂CH₃ | H |
| C.66 | 0 | NHCH(CH₃)CH₂SCH₃ | H |
| C.67 | 0 | NHCH(CH₃)CH₂S(O)CH₂CH₃ | H |
| C.68 | 0 | HN-CH(CH₃)CH₂-(morpholin-4-yl) | H |
| C.69 | 0 | HN-(tetrahydrofuran-3-yl) | H |
| C.70 | 0 | HN-(pyrrolidin-3-yl) | H |
| C.71 | 0 | HNCH(CH₃)CH₂CH₂N=C(NH₂)NH₂ | H |
| C.72 | 0 | NHCH(CH₃)CH₂CH₂O-(3-pyridyl) | H |

TABLE C-continued

| No. | J | R$_1$ | R$_2$ |
|---|---|---|---|
| C.73 | 0 | NHCH(CH$_3$)CH$_2$-(5-pyrimidyl) | H |
| C.74 | 0 | NHCH(CH$_3$)CH$_2$-(5-pyrimidyl) | H |
| C.75 | 0 | NHCH(CH$_3$)CH$_2$CH$_2$O-(2-thiazolyl) | H |
| C.76 | 0 | NHCH(CH$_3$)CH$_2$-(4-thiazolyl) | H |
| C.77 | 0 | NHCH(CH$_3$)CH$_2$-(2-furyl) | H |
| C.78 | 0 | NHCH(CH$_2$CH$_3$)CH$_2$CH$_2$O-(1-[1,2,4-triazolyl]) | H |
| C.79 | 0 | NHCOCH(CH$_3$)CH=CH$_2$ | H |
| C.80 | 0 | N(CH$_3$)CONHCH$_2$CH$_3$ | H |
| C.81 | 0 | NHCON(CH$_3$)CH(CH$_3$)$_2$ | H |
| C.82 | 0 | NH-(1-methylpyrrolidin-3-yl) | H |
| C.83 | 0 | N=CHNH$_2$ | H |
| C.84 | 0 | N=CHN(CH$_3$)$_2$ | H |
| C.85 | 0 | N=C(CH$_3$)N(CH$_3$)$_2$ | H |
| C.86 | 0 | (1-methyl-2-imino-imidazolidine) | H |
| C.87 | 0 | N=C(NH(CH$_3$))N(CH$_3$)$_2$ | H |
| C.88 | 0 | (1,4-dimethyl-2-imino-imidazolidine) | H |
| C.89 | 0 | NHCH$_2$CH$_2$-(1,2,4)-triazol-1-yl | H |
| C.90 | 0 | NHCH$_2$CH$_2$-(1-imidazolyl) | H |
| C.91 | 0 | oxazolidin-2-one | H |
| C.92 | 0 | 4-methyl-oxazolidin-2-one | H |
| C.93 | 0 | 4-ethyl-oxazolidin-2-one | H |
| C.94 | 0 | 4-isopropyl-yl-oxazolidin-2-one | H |
| C.95 | 0 | 5-methyl-yl-oxazolidin-2-one | H |
| C.96 | 0 | 4,5-dimethyl-yl-oxazolidin-2-one | H |
| C.97 | 0 | 4,4-dimethyl-yl-oxazolidin-2-one | H |
| C.98 | 0 | oxazolidine-2-thione | H |
| C.99 | 0 | 4-methyl-2-yl-oxazolidine-2-thione | H |
| C.100 | 0 | imidazolidin-2-one | H |
| C.101 | 0 | 5-methyl-imidazolidin-2-one | H |
| C.102 | 0 | 2-oxo-2lambda*4*-[1,2,3]oxathiazolidin | H |
| C.103 | 0 | 4-methyl-2-oxo-2lambda*4*-[1,2,3]oxathiazolidin | H |
| C.104 | 0 | 4-methyl-[1,3]oxazinane | H |
| C.105 | 0 | 2-methyl-4-morpholine-3,5-dione | H |
| C.106 | 0 | 3-methyl-piperidine-2,6-dione | H |
| C.107 | 0 | 4,5-dimethyl-3[1,3]oxazinan-2-one | H |
| C.108 | 0 | 4-morpholine-3,5-dione | H |
| C.109 | 0 | (4-methyl-2-oxo-oxazolidin-5-yl)-acetonitrile | H |
| C.110 | 0 | [1,3]oxazinane-2-one | H |
| C.111 | 0 | [1,3]oxazinane-2-one | CH$_2$OCH$_2$CH$_3$ |
| C.112 | 0 | 4-methyl-[1,3]oxazinan-2-one | CH$_2$OCH$_2$CH$_3$ |
| C.113 | 0 | 3-methyl-piperidine-2,6-dione | CH$_2$OCH$_2$CH$_3$ |
| C.114 | 0 | 5-methyl-imidazolidin-2-one | CH$_2$OCH$_2$CH$_3$ |
| C.115 | 0 | 4-methyl-oxazolidin-2-one | CH$_2$OCH$_2$CH$_3$ |
| C.116 | 0 | N=C(CH$_3$)N(CH$_3$)$_2$ | CH$_2$OCH$_2$CH$_3$ |
| C.117 | 1 | HN-(pyrrolidin-3-yl)-NH | H |
| C.118 | 1 | NHCH(CH$_2$CH$_3$)CH$_2$CH$_2$O-(1-[1,2,4-triazolyl]) | H |
| C.119 | 1 | NHCH(CH$_3$)CH$_2$OCH$_3$ | H |
| C.120 | 1 | NHCH(CH$_3$)CH$_2$CH$_2$OCH$_3$ | H |
| C.121 | 1 | NHCH(CH$_2$CH$_3$)CH$_2$CN | H |
| C.122 | 0 | N[C(O)CH$_2$CH$_2$OCH$_3$]NH(CH$_3$) | CH$_2$OCH$_2$CH$_3$ |

TABLE C-continued

| No. | J | R₁ | R₂ |
|---|---|---|---|
| C.123 | 0 | [1,3]oxazinane-2-one | $CH_2SCH_2CH_3$ |
| C.124 | 0 | 4-methyl-[1,3]oxazinan-2-one | $CH_2SCH_2CH_3$ |
| C.125 | 0 | 3-methyl-piperidine-2,6-dione | $CH_2SCH_2CH_3$ |
| C.126 | 0 | 5-methyl-imidazolidin-2-one | $CH_2SCH_2CH_3$ |
| C.127 | 0 | $N[C(O)CH_2CH_2OCH_3]NH(CH_3)$ | $CH_2CH{=}CH_2$ |
| C.128 | 0 | $NHCH(CH_2CH_3)CH_2CN$ | $CH_2CH{=}CH_2$ |
| C.129 | 0 | $NHCH(CH_3)CH_2CH_2OCH_3$ | $CH_2CH{=}CH_2$ |
| C.130 | 0 | $NHCH(CH_3)CH_2OCH_3$ | $CH_2CH{=}CH_2$ |
| C.131 | 0 | $NHCH(CH_2CH_3)CH_2CH_2O\text{-}(1\text{-}[1,2,4\text{-}triazolyl])$ | $CH_2CH{=}CH_2$ |
| C.132 | 0 |  | $CH_2OCH_2CH_3$ |
| C.133 | 0 | $N{=}C(CH_3)N(CH_3)_2$ | $CH_2CH{=}CH_2$ |
| C.134 | 0 | 4-methyl-oxazolidin-2-one | $C({=}O)CH_2CH_2CH_3$ |
| C.135 | 0 | 3-methyl-piperidine-2,6-dione | $SO_2CH_3$ |
| C.136 | 0 |  | $CH_2SCH_2CH_3$ |
| C.137 | 0 | $NHCH(CH_2CH_3)CH_2CN$ | $CH_2(OCH_2CH_2)OCH_3$ |
| C.138 | 0 | $NHCH(CH_3)CH_2OCH_3$ | $CH_2OCH_2Ph$ |
| C.139 | 0 | 4-methyl-oxazolidin-2-one | $CH_2OCH_2Ph$ |
| C.140 | 0 | [1,3]oxazinane-2-one | $C({=}O)CH_2OCH_3$ |
| C.141 | 0 | 4-methyl-[1,3]oxazinan-2-one | $C({=}O)CH(CH_3)_2$ |
| C.142 | 0 | $N{=}C(CH_3)N(CH_3)_2$ | $CH_2OCH_2Ph$ |
| C.143 | 0 | $NHCH(CH_3)CH_2CH_2OCH_3$ | $C({=}O)CH_2OCH_3$ |
| C.144 | 0 | 5-methyl-imidazolidin-2-one | $SO_2CF_3$ |
| C.145 | 0 | $NHCH(CH_2CH_3)CH_2CH_2O\text{-}(1\text{-}[1,2,4\text{-}triazolyl])$ | $CH_2C{\equiv}CH_3$ |
| C.146 | 0 | $N[C(O)CH_2CH_2OCH_3]NH(CH_3)$ | $CH_2C{\equiv}CH_3$ |

Further compounds of general structure I are those where A and A' are both CH and the values of $R_3$ to $R_6$ corresponds with a line of Table B and the values of j, $R_1$ and $R_2$ correspond with a line of Table C.

Further compounds of general structure I are those where A is CH and A' is N and the values of $R_3$ to $R_6$ corresponds with a line of Table B and the values of j, $R_1$ and $R_2$ correspond with a line of Table C.

The compounds according to the invention may be prepared according to known methods. The procedures for the preparation of compounds of formula I where A is CH and A' is N are detailed in WO 01/93682 and WO 02/053560. These procedures may be modified for compounds where A and A' are both N according to the procedures described in WO-0125220 A1 and in Libermann et al, Bull. Soc. Chim. Fr.; 1958, 687 and in the Examples. For compounds where A and A' are both CH the known procedures are illustrated in the Examples.

The invention also relates to compositions which comprise the compounds of the formula I, or a salt thereof, as an active component, in particular plant-protecting compositions, and also to their use in the agricultural sector or related areas.

Active compounds of the formula I are customarily used in the form of compositions and may be added, simultaneously or successively, to the surface or plant to be treated together with additional active compounds. These additional active compounds may be either fertilizers, trace element-supplying agents or other preparations which influence plant growth. It is also possible, in this context, to use selective herbicides, such as insecticides, fungicides, bactericides, nematicides or molluscicides, or mixtures of several of these preparations, additionally, where appropriate, together with excipients, surfactants or other administration-promoting additives which are customary in formulation technology (designated collectively as carrier materials herein).

Suitable excipients and additives may be solid or liquid and are those substances which are appropriate in formulation technology, for example natural or regenerated minerals, solvents, dispersants, wetting agents, adhesives, thickening agents, binding agents or fertilizers.

A preferred method for applying a compound of formula I, or an agrochemical composition which comprises at least one of these compounds, is administration to the leaves (foliar application). The frequency and rate of administration depend upon the risk of infestation by the corresponding pathogen. The compounds of formula I can, however, also penetrate the plant through the roots via the soil (systemic action). If the locus of the plant is impregnated with a liquid formulation or if the substances are introduced in solid form into the soil, e.g. in the form of granules (soil application). In paddy rice crops, such granules can be applied in metered amounts to the flooded rice fields. In order to treat seeds, the compounds of formula I can, however, also be applied to the seeds (coating), either by impregnating the grains or tubers with a liquid formulation of the active ingredient, or by coating them with a solid formulation.

Advantageous rates of application are in normally from 5 g to 2 kg of active ingredient (a.i.) per hectare (ha), preferably from 10 g to 1 kg of a.i./ha, especially from 20 g to 600 g a.i./ha. When the compound are used as seed dressings, dosages of from 10 mg to 1 g of active ingredient per kg seed are advantageously employed. The agrochemical compositions generally comprise 0.1 to 99% by weight, preferably 0.1 to 95% by weight, of a compound of formula I, 99.9 to 1% by weight, preferably 99.8 to 5% by weight, of a solid or liquid adjuvant and 0 to 25% by weight, preferably 0.1 to 25% by weight, of a surfactant. Whereas commercial products will preferably be formulated as concentrates, the end user will normally employ dilute formulations.

The compositions may also comprise further auxiliaries, such as fertilizers and other active ingredients for obtaining special desirable biological effects.

The compounds of formula I may be used preventatively and/or curatively in the sector of agronomics and related technical areas as active ingredients for controlling plant pests. The active ingredients of formula I according to the invention are notable for their good activity even at low concentrations, for their good plant tolerance and for their environmentally friendly nature. They have very advantageous, especially systemic, properties and may be used to protect a plurality of cultivated plants. Using the active ingredients of formula I on plants or plant parts (fruit, flowers, leaves, stems, tubers, roots) of various crops, the pests appearing can be controlled or destroyed, whereby the parts of plants which grow later also remain protected, e.g. from phytopathogenic microorganisms.

The compounds I may additionally be used as a dressing to treat seeds (fruits, tubers, corns) and plant cuttings to protect against fungal infections and against phytopathogenic fungi occurring in the soil.

The compounds I are effective for example against the following classes of related phytopathogenic fungi: Fungi imperfecti (e.g. *Botrytis, Pyricularia, Helminthosporium, Fusarium, Septoria, Cercospora* and *Alternaria*); Basidiomycetes (e.g. *Rhizoctonia, Hemileia, Puccinia*); Ascomycetes (e.g. *Venturia* and *Erysiphe, Podosphaera, Monilinia, Uncinula*) and Oomycetes (e.g. *Phytophthora, Pythium, Plasmopara*).

Target crops for the plant-protecting usage in terms of the invention are for example the following plant cultivars: cereals (wheat, barley, rye, oats, rice, maize, sorghum and related species); beet (sugar beet and fodder beet); pome, stone and berry Suit (apples, pears, plums, peaches, almonds, cherries, strawberries, raspberries and blackberries); legumes (beans, lentils, peas, soya); oil crops (rape, mustard, poppy, olives, sunflowers, coconut, castor oil, cocoa, peanut); cucumber plants (squashes, cucumber, melons); citrus fruits (oranges, lemons, grapefruits, mandarines); vegetables (spinach, lettuce, asparagus, cabbage varieties, carrots, onions, tomatoes, potatoes, paprika); laurels (avocado, cinnamonium, camphor) and plants such as tobacco, nuts, coffee, aubergines, sugar cane, tea, pepper, vines, hops, bananas and natural rubber plants, as well as ornamental plants.

Further areas of application for the active ingredients according to the invention are the protection of stores and material, where the storage matter is protected against putrescence and mould.

Furthermore the fungicidal activity allows the compounds according to present invention tob employed in controlling fungi in related areas, e.g. in protection of technical materials, including wood and wood related technical products, in food storage and in hygiene management The compounds I are used in unchanged form or preferably together with customary excipients in formulation techniques. To this end, they are conveniently processed in known manner e.g. into emulsion concentrates, coatable pastes, directly sprayable or diluable solutions, diluted emulsions, wettable powders, soluble powders, dusts or granules, e.g. by encapsulation into for example polymeric materials. As with the type of medium, the application processes, such as spraying, atomizing, dusting, scattering, coating or pouring are similarly chosen according to the desired aims and the prevailing conditions.

Suitable substrates and additives may be solid or liquid and are useful substances in formulation techniques, e.g. natural or regenerated mineral substances, dissolving aids, dispersants, wetting agents, tackifiers, thickeners or binding agents.

The compounds of formula I may be mixed with further active ingredients, e.g. fertilizers, ingredients providing trace elements or other active ingredients used in the plant protection science, especially further fungicides. In doing so, in some cases synergistic enhancement of the biological effects may occur.

Preferred active ingredients advantageous as additives to the compositions comprising the active ingredient of formula I are:

Azoles, such as azaconazole, BAY 14120, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, simeconazole, tebuconazole, tetraconazole, triadimefon, triadimenol, triflumizole, triticonazole; pyrimidinyl carbinole, such as ancymidol, fenarimol, nuarimol; 2-amino-pyrimidines, such as bupirimate, dimethirimol, ethirimol; morpholines, such as dodemorph, fenpropidine, fenpropimorph, spiroxamine, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozoline; carboxamides, such as carboxin, fenfuram, flutolanil, mepronil, oxycarboxin, thifluzamide; guanidines, such as guazatine, dodine, iminoctadine; strobilurines, such as azoxystrobin, kresoximmethyl, metominostrobin, SSF-129, trifloxystrobin, picoxystrobin, BAS 500F (proposed name pyraclostrobin), BAS 520; dithiocarbamates, such as ferbam, mancozeb, maneb, metiram, propineb, thiram, zineb, ziram; N-halomethylthiotetrahydrophthalimides, such as captafol, captan, dichlofluanid, fluoromides, folpet, tolyfluanid; Cu-compounds, such as Bordeaux mixture, copper hydroxide, copper oxychloride, copper sulfate, cuprous oxide, mancopper, oxine-copper; nitrophenol-derivatives, such as dinocap, nitrothal-isopropyl; organo-p-derivatives, such as edifenphos, iprobenphos, isoprothiolane, phosdiphen, pyrazophos, tolclofos-methyl; various others, such as acibenzolar-S-methyl, anilazine, benthiavalicarb, blasticidin-S, chinomethionate, chloroneb, chlorothalonil, cyflufenamid, cymoxanil, dichlone, diclomezine, dicloran, diethofencarb, dimethomorph, SYP-LI90 (proposed name: flumorph), dithianon, ethaboxam, etridiazole, famoxadone, fenamidone, fenoxanil, fentin, ferimzone, fluazinam, flusulfamide, fenhexamid, fosetyl-aluminium, hymexazol, iprovalicarb, IKF-916 (cyazofamid), kasugamycin, methasulfocarb, metrafenone, nicobifen, pencycuron, phthalide, polyoxins, probenazole, propamocarb, pyroquilon, quinoxyfen, quintozene, sulfur, triazoxide, tricyclazole, triforitie, validamycin, zoxamide (RH7281).

One preferred method of application of an active ingredient of formula I or of an agrochemical composition containing at least one of these active ingredients is foliar application. The frequency and amount of application depend on the severity of the attack by the pathogen in question. However, the active ingredients I may also reach the plants through the root system via the soil (systemic action) by drenching the locus of the plant with a liquid preparation or by incorporating the substances into the soil in solid form, e.g. in the form of granules (soil application). In rice cultivations, these granules may be dispensed over the flooded paddy field. The compounds I may however also be applied to seed grain to treat seed material (coating), whereby the grains or tubers are either drenched in a liquid preparation of the active ingredient or coated with a solid preparation.

The compositions are produced in known manner, e.g. by intimately mixing and/or grinding the active ingredient with extenders such as solvents, solid carriers and optionally surfactants.

Favourable application rates are in general 1 g to 2 kg of active substance (AS) per hectare (ha), preferably 10 g to 1 kg AS/ha, especially 20 g to 600 g AS/ha. For usage as a seed dressing, it is advantageous to use dosages of 10 mg to 1 g active substance per kg of seed grain.

While concentrated compositions are preferred for commercial usage, the end user normally uses diluted compositions.

Formulations may be prepared analogously to those described for example in WO 97/33890.

The invention is illustrated by the follwing Examples:

EXAMPLE 1

Step a. Synthesis of 2,2'-Dichloro-[4,4']-bipyridinyl

Phosphorus oxychloride (100 ml) was heated to 70° C. and pyridine (7.1 ml), PCl$_5$ (8.1 g) and [4,4']bipyridinyl 1,1'dioxide (6.4 g) were added portion wise over 30 min. The mixture was then heated to reflux for 48 hours, cooled. The cooled mixture was poured drop wise onto ice with vigorous stirring, then still with ice cooling brought to pH 12-14 by adding 10M NaOH. Mixture was extracted with ethyl acetate, dried over Na$_2$SO$_4$ and concentrated under reduced pressure. The residue was purified by passing the crude mixture down Kieselgel using 5:95 THF:CH$_2$Cl$_2$ as the eluent.

Melting point: 239-240° C.

Step b. Synthesis of (2'-Chloro-[4,4']bipyridinyl-2-yl)-(2-methoxy-1-methyl-ethyl)-amine Xantphos (32 mg), and Pd$_2$(dba)$_3$ (25 mg) were suspended in toluene (8 ml) and stirred under argon for 10 mins, then 2,2'-dichloro-[4,4']-bipyridinyl (250 mg), 2-amino-1-methoxypropane (0.117 ml) and sodium tert-butoxide (150 mg) were added. The mixture stirred at 60° C. for 6 hours then cooled to room temp, poured onto water and extracted with ethyl acetate, dried over Na$_2$SO$_4$ and concentrated under reduced pressure. The residue was purified by passing the crude mixture down Kieselgel using a gradient of hexane and ethyl acetate as the eluent.

NMR in CDCl3, 1.3 ppm,d,3H; 3.4 ppm,s,3H; 3.5 ppm,m, 2H; 4.15 ppm, m,1H; 5.0 ppm, d,1H; 6.6 ppm,s,1H; 6.75 ppm,d,1H; 7.4 ppm,d,1H; 7.52 ppm,s,1H; 8.18 ppm,d,1H; 8.5 ppm,d,1H.

Step c. Synthesis of N*2'*-(3-Chloro-phenyl)-N*2*-(2-methoxy-1-methyl-ethyl)-[4,4']bipyridinyl-2,2'-diamine Pd(OAc)$_2$ (8 mg) and BINAP (16 mg) were suspended in toluene (10 ml) and stirred under argon for 10 mins, then (2'-Chloro-[4,4']bipyridinyl-2-yl)-(2-methoxy-1-methylethyl)-amine (90 mg), 3-chloroaniline (124 mg) and potassium carbonate (890 mg) were added. The mixture was stirred at 110° C. for 5 hours then cooled to room temp, poured onto water and extracted with ethyl acetate, dried over Na$_2$SO$_4$ and concentrated under reduced pressure. The residue was purified by passing the crude mixture down Kieselgel using 1:99 THF:CH$_2$Cl$_2$ as the eluent.

Melting point: 110° C.

EXAMPLE 2

Step a

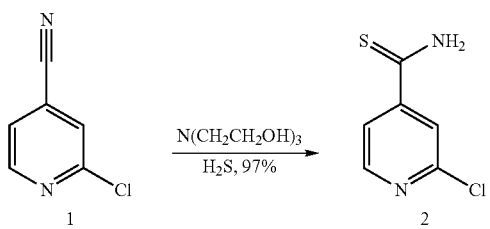

To a solution/suspension of 1 (10.0 g; 72 mmol) in ethanol (100 mL) was added triethanolamine (4.0 mL; 39.8 mmol). H$_2$S was then passed through the solution. After a few minutes precipitation of a yellow solid was observed. The reaction was continued until TLC showed complete conversion (30 min). The reaction mixture was poured into ice-water (~300 mL), which resulted in precipitation of product. After stirring for 15 min the solid was filtered off, washed with water and dried (vacuum, P$_2$O$_5$). Yield: 12.1 g (97%).

Step b

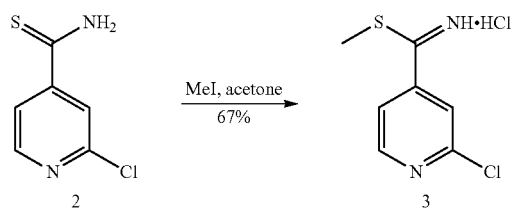

To a solution of 2 (7.0 g; 40.6 mmol) in acetone (170 mL) was added iodomethane (12.6 mL; 202 mmol) and the reaction mixture was stirred in the dark for 3 days. The yellow precipitate was filtered off and washed with acetone and ether (2×) and dried. Yield: 8.57 g (67%).

Step c

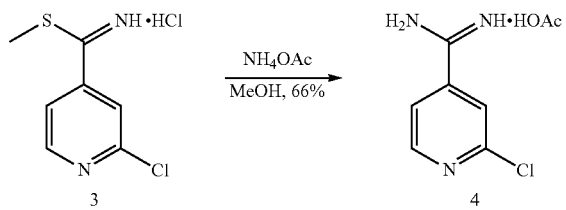

To a solution of 3 (12.3 g; 39.1 mmol) in methanol (250 mL) was added ammonium acetate (6.2 g; 80.4 mmol) and the mixture was stirred at 70° C. (oil bath temp) overnight (20 h). The reaction mixture was evaporated to dryness, which gave a white residue. 2-Propanol (175 mL) was added and the suspension was stirred for 30 min. The product was filtered off and washed with 2-propanol and ether (3×) and dried. Yield: 5.6 g (66%).

Step d

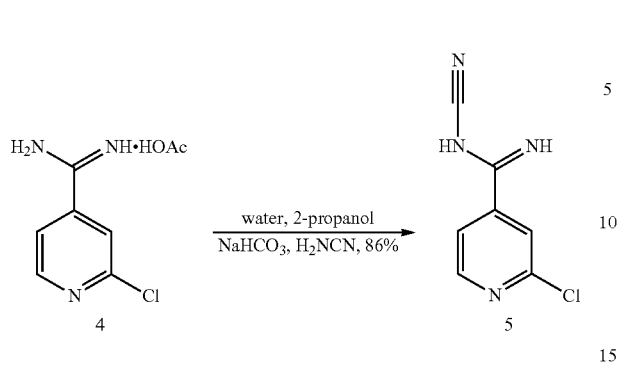

To 4 (5.60 g; 26.0 mmol) were added sequentially water (250 mL), 2-propanol (100 mL), NaHCO₃ (8.53 g; 0.10 mol) and cyanamide (50 wt. % in water; 5.9 mL; 75.9 mmol) and the mixture was stirred at room temp overnight (20 h). The product was filtered off and washed with 2-propanol (2×) and ether (2×) and dried. Yield: 4.06 g (86%).

Step e

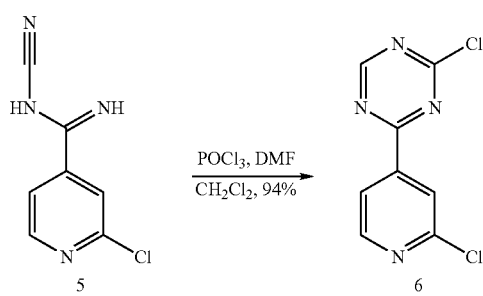 [SMILES: N#CNC(=N)c1ccnc(Cl)c1 ; Clc1cc(-c2ncnc(Cl)n2)ccn1]

A solution of DMF (1.0 mL; 12.9 mmol) in CH₂Cl₂ (90 mL) was cooled in ice under N₂ and to this was added POCl₃ (1.3 mL; 13.9 mmol). The mixture was stirred at 0° C. for 30 min. To this was added portion-wise 5 (1.60 g; 8.9 mmol) in about 5 min. After complete addition stirring was continued for 5 h at room temp. The almost clear solution was diluted with CH₂Cl₂ (150 mL) and the organic layer was washed with sat. NaHCO₃ (2×200 mL) and water (200 mL), dried (NaSO₄) and evaporated to dryness. Yield: 1.89 g (94%) of a pale yellow solid. NMR: (D6DMSO, ppm) 8.72 (1H), 8.6 (1H), (0.11 (2H).

Step f

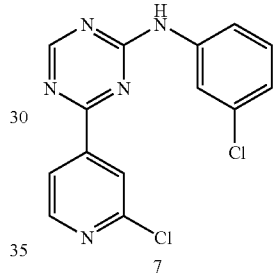 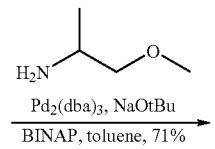

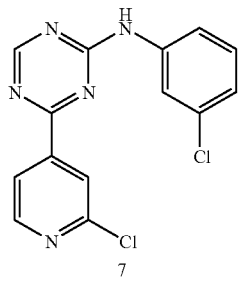

To a suspension of 6 (256 mg; 1.1 mmol) in 2-propanol (5 mL) was added 3-chloroaniline (192 μl; 1.8 mmol) and the suspension was stirred at room temp overnight. The product was filtered off, washed with 2-propanol and dried. Yield: 305 mg (85%).

Step g

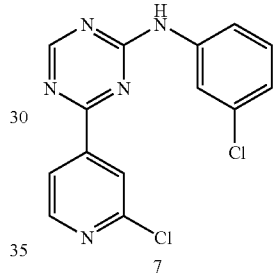

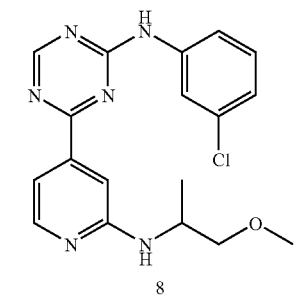

To a suspension of 7 (318 mg; 1.0 mmol) in dry toluene (4 mL) were added BINAP (50 mg; 0.080 mmol), Pd₂(dba)₃ (25 mg; 0.027 mmol), NaOtBu (220 mg; 2.3 mmol) and 2-amino-1-methoxypropane (316 μl; 3.0 mmol) and the mixture was degassed with argon for 5 min. The reaction mixture was heated at 90° C. under N₂ for 3 h, after which TLC analyses indicated that the reaction was complete. The reaction mixture was partitioned between ethyl acetate (25 mL) and water (25 mL), the layers were separated and the water layer was extracted with ethyl acetate (3×25 mL). The combined organic layers were dried (Na2SO4) and concentrated. The crude product was purified by column chromatography (SiO2, first: EtOAcA/Heptane, 1/1; then pure EtOAc). Yield: 266 mg (71%); mp: 158-159° C.

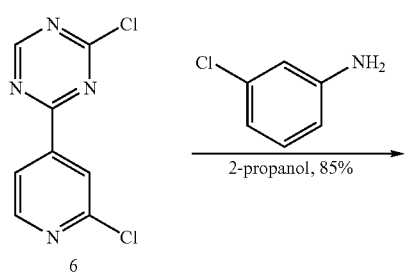

EXAMPLE 3

Synthesis of N*2'*-(4-Chloro-phenyl)-N*2*-(2-methoxy-1-methyl-ethyl)-[4,4']bipyridinyl-2,2'-diamine

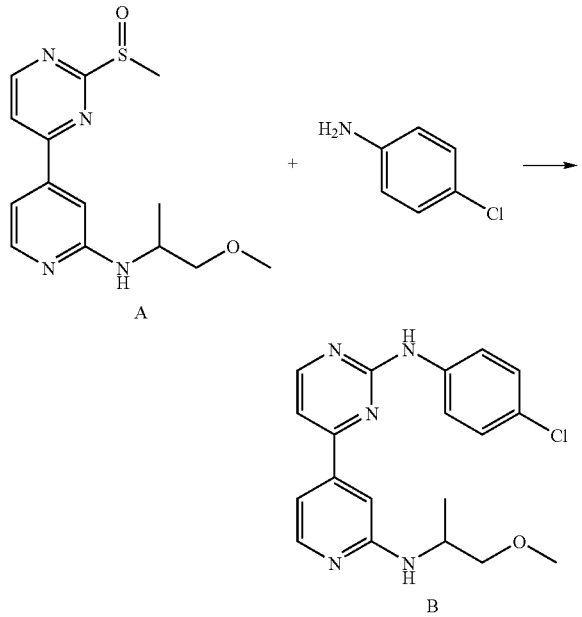

3-Chloroaniline (0.13 ml) was diluted with THF (5 ml) and cooled to 0° C. LiN(TMS)$_2$ (1.3 ml of a 1M solution in THF) was added dropwise and stirred at 0° C. for 30 minutes. 0.20 g of A was diluted with THF (2 ml) and added dropwise to the reaction mixture and stirring was continued at 0° C. for a further 30 mins. The ice bath was then removed and the mixture was stirred at room temp for 3 hours. For work up the reaction mixture was poured into sat NaCl solution and extracted with ethyl acetate 3 times, dried over Na$_2$SO$_4$, filtered and concentrated. The desired compound was optained as a pale yellow powder, mp: 150-153° C.

In the following, examples of test systems in plant protection are provided which demonstrate the efficiency of the compounds of the formula I (designated as "active ingredient" or "test compounds"):

BIOLOGICAL EXAMPLES

Example B-1

Effect Against *Puccinia graminis* on Wheat (Brownrust on Wheat)

a) Residual Protective Activity 1 week old wheat plants cv. Arina are treated with the formulated test-compound (0.02% active substance) in a spray chamber. Two days after application wheat plants are inoculated by spraying a spore suspension (1×10$^5$ ureidospores/ml) on the test plants. After an incubation period of 1 day at +20° C. and 95% relative atmospheric humidity (r. h.) plants are kept for 9 days at +20° C. and 60% r.h. in a greenhouse. The disease incidence is assessed 10 days after inoculation.

At the indicated concentration compounds A1.03, A1.05, A1.10, A1.11, A1.20, A1.21, A1.45, A1.60, A1.66, A1.72, A1.79, A1.84, A1.103, A1.116, A1.118, A.1.123 and A1.128 exhibited over 70% control of the fungal infection in this test.

Example B-2

Effect Against *Plasmopara viticola* on Grapevine (Grape Downy Mildew)

5 week old grape seedlings cv. Gutedel are treated with the formulated test compound (0.02% active substance) in a spray chamber. One day after application grape plants are inoculated by spraying a sporangia suspension (4×10$^4$ sporangia/ml) on the lower leaf side of the test plants. After an incubation period of 6 days at +22° C. and 95% r. h. in a greenhouse the disease incidence is assessed.

At the indicated concentration compounds A.1.45 and A1.10 exhibited over 70% control of the fungal infection in this test.

Example B-3

Residual Protective Activity Against *Venturia inaegualis* on Apples (Scab on Apple)

4 week old apple seedlings cv. McIntosh are treated with the formulated test compound (0.02% active substance) in a spray chamber. One day after application apple plants are inoculated by spraying a spore suspension (4×10$^5$ conidia/ml) on the test plants. After an incubation period of 4 days at +20° C. and 95% r. h. the plants are transferred to standard greenhouse conditions at 20 and 60% r.h. where they stayed for 2 days. After another 4 day incubation period at +20° C. and 95% r. h. the disease incidence is assessed.

At the indicated concentration compounds A1.03, A1.05, A1.10, A1.11, A1.12, A1.20, A1.21, A1.45, A1.60, A1.66, A1.72, A1.84, A1.116, A1.118, A.1.123, A1.23, A1.22, A1.64, A1.16 and A1.15 exhibited over 70% control of the fungal infection in this test.

Example B4

Effect Against *Erysiphe graminis* on Barley (Powdery Mildew on Barley a) Residual Protective Activity Barley plants, cv. Regina of approximately 8 cm height were treated with the formulated test compound (0.02% active substance) in a spray chamber and duste 2 days after inoculation with conidia of the fungus. The infected plants are placed in a greenhouse at +20° C. 6 days after infection, the fungal attack was evaluated.

At the indicated concentration compounds A1.03, A1.05, A1.10, A1.11, A1.12, A1.20, A1.21, A1.45, A1.60, A1.66, A1.72, A1.84, A1.116, A1.118, A.1.123, A1.23, A1.22, A1.64, A1.16 and A1.15 exhibited over 70% control of the fungal infection in this test.

Example B-5

Effect Against *Botrytis cinerea*/Tomato (*Botrytis* on Tomatoes)

4 week old tomato plants cv. Roter Gnom are treated with the formulated test compound 0.02% active substance) in a spray chamber. Two days after application tomato plants are inoculated by spraying a spore suspension ($1\times10^5$ conidia/ml) on the test plants. After an incubation period of 4 days at +20° C. and 95% r. h. in a greenhouse the disease incidence is assessed.

At the indicated concentration compounds A1.03, A1.05, A1.10, A1.11, A1.12, A1.20, A1.21, A1.45, A1.60, A1.66, A1.72, A1.79, A1.84, A1.116, A1.118, A.1.123, A1.23, A1.22, A1.128, A1.64, A1.16 and A1.15 exhibited over 70% control of the fungal infection in this test.

Example B-6

Effect Against *Pyricularia oryzae*/Rice (Rice Blast)

3 week old rice plants cv. Sasanishiki are treated with the formulated test compound (0.02% active substance) in a spray chamber. Two days after application rice plants are inoculated by spraying a spore suspension ($1\times10^5$ conidia/ml) on the test plants. After an incubation period of 6 days at +25° C. and 95% r. h. the disease incidence is assessed.

At the indicated concentration compounds A1.03, A1.05, A1.10, A1.11, A1.12, A1.20, A1.21, A1.45, A1.60, A1.66, A1.72, A1.84, A1.116, A1.118, A.1.123, A1.23, A1.22, A1.64, A1.16 and A1.15 exhibited over 70% control of the fungal infection in this test.

Example B-7

Effect Against *Pyrenophora teres* (*Helminthosporium*)/Barley (Net Blotch on Barley)

1 week old barley plants cv. Regina are treated with a formulated test compound (0.02% active substance) in a spray chamber. Two days after application barley plants are inoculated by spraying a spore suspension ($3\times10^4$ conidia/ml) on the test plants. After an incubation period of 2 days at +20° C. and 95% r.h. the disease incidence is assessed.

At the indicated concentration compounds A1.03, A1.05, A1.10, A1.11, A1.12, A1.20, A1.21, A1.45, A1.60, A1.66, A1.72, A1.79, A1.84, A1.103, A1.116, A1.118, A.1.123, A1.23, A1.22, A1.64, A1.16, A1.15, A1.76, A1.87, A1.81, A1.130, A1.150, A1.151, A1.152, A1.153 and A1.96 exhibited over 70% control of the fungal infection in this test.

Example B-8

Effect Against *Septoria nodorum*/Wheat (*Septoria* Leaf Spot on Wheat)

1 week old wheat plants cv. Arina are treated with a formulated test compound (0.02% active substance) in a spray chamber. One day after application wheat plants are inoculated by spraying a spore suspension ($6\times10^5$ conidia/ml) on the test plants. After an incubation period of 1 day at +22° C. and 95% r.h. plants are kept for 7 days at +22° C. and 60% r.h. in a greenhouse. The disease incidence is assessed 8 days after inoculation.

At the indicated concentration compounds A1.03, A1.05, A1.10, A1.11, A1.12, A1.20, A1.21, A1.45, A1.60, A1.66, A1.72, A1.79, A1.84, A1.103, A1.116, A1.118, A.1.123, A1.23, A1.22, A1.128, A1.64, A1.16, A1.15, A1.76, A1.87, A1.81 and A1.96 exhibited Over 70% control of the fungal infection in this test.

What is claimed is:

1. A method of controlling and preventing an infestation of crop plants by phytopathogenic microorganisms, which comprises the application to the plant or parts of plants or to the locus thereof as active ingredient an N-phenyl-[(4-pyridyl)-azinyl]-amine derivative of the formula I

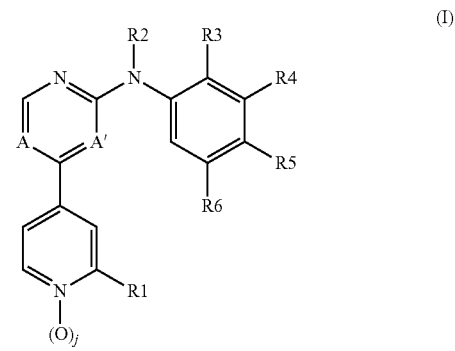

wherein
A and A' are both N or A and A' are both CH or A is CH and A' is N;
j is 0 or 1
$R_1$ is
a) hydrazino, that is unsubstituted or one- to threefold substituted by optionally substituted alkyl and/or optionally substituted acyl,
b) cyclohexylamino, tetrahydro-4H-pyranyl-4-amino, pyrrolidine-3-amino, 2- or 3-tetrahydro-furylamino, all optionally substituted by amino, hydroxy, alkoxy, alkyl or alkoxyalkyl,
c) piperazinyl that is optionally substituted by amino, amino-lower alkyl, hydroxy, alkoxy, alkyl or alkoxyalkyl,
d) morpholinyl that is optionally substituted by amino, amino-lower alkyl, hydroxy, alkoxy, alkyl or alkoxyalkyl,
e) amino or mono- or di-(lower alkyl)amino wherein the lower alkyl moieties are unsubstituted or substituted by one or more substitutents independently selected from the group consisting of unsubstituted amino, N-mono- or N,N-di-(lower alkyl)-amino, (lower alkoxy)-lower alk-oxy, lower alkoxycarbonylamino, hydroxy-lower alkoxycarbonylamino, lower alkoxy-lower alkoxycarbonylamino, morpholinyl, hydroxy-lower alkylamino, cyano, halogen, oxo, hydroximino, alkoximino, optionally substituted hydrazono, lower alkenyl, lower alkynyl, guanidyl, lower alkanoylamino, hydroxy-lower alkanoylamino, lower alkoxy-lower alkanoylamino, halo-lower alkanoylamino, lower alkylaminocarbonylamino, hydroxy-lower alkylaminocarbonylamino, lower alkoxy-lower alkylaminocarbonylamino, amidino, di-lower-alkylamino-cyclohexyl, carboxy, lower alkoxycarbonyl, hydroxy-lower alkoxycarbonyl, lower alkoxy-lower alkoxycarbonyl, lower alkylcarbonyldioxy (=lower alkoxycarbonyloxy), hydroxy-lower alkoxycarbonyloxy, lower alkoxy-lower alkoxycarbonyloxy, lower alkanoyloxy, halo-lower alkanoyloxy, hydroxy-lower alkanoyloxy, lower alkoxy-lower alkanoyloxy, carbamoyl, N-mono- or N,N-di-lower alkylcarbamoyl, N-(hydroxy-lower alkyl)carbamoyl, N-lower alkyl-N-hydroxy-lower alkyl-carbamoyl, N,N-di-(hydroxy-lower alkyl)-carbamoyl, N-hydroxy-carbamoyl, hydroxy, lower alkoxy, lower alkenyloxy, lower alkinyloxy, lower haloalkoxy, lower alkylthio, lower alkylsulfoxyl, lower alkylsulfonyl, lower alkoxysilyl, 4-tetrahydro-4H-pyranyl, 3-pyrrolidinyl, 2- or 3-tetrahydrofuryl, 2- or 3-dihydrofuryl, piperazinyl, lower alkanoyl-piperazinyl, optionally substituted heteroaryl and optionally substituted heteroaryloxy, f) optionally substituted alkanoylamino, optionally substituted alkenoylamino, optionally substituted alkynoylamino, optionally substituted mono- or di-alkylaminocarbonylamino, optionally substituted alkoxycarbonylamino, optionally substituted mono- or di-alkylaminosulfonylamino, optionally substituted mono- or di-alkylaminosulfoxylamino, g) N-(optionally substituted alkyl)-N-(optionally substituted lower alkanoyl)-amino, h) N-(optionally substituted alkyl)-N-(optionally substituted alkoxycarbonyl)-amino, i) N-(optionally substituted alkyl)-N—(N',N'-mono- or di-[optionally substituted alkyl]-aminocarbonyl)-amino, j) N=C($R_7$,$R_8$) wherein $R_7$ is hydrogen, alkyl, amino, mono- or di-alkylamino and $R_8$ is amino, mono- or dialkylamino or wherein $R_7$ and $R_8$, together with the binding carbon atom, form a saturated five- to seven-membered ring with 0, 1 or 2 ring nitrogen atoms that is optionally substituted by one or more substituents, k) an optionally substituted 4 to 7 membered heterocyclyl group containing one or two nitrogen, oxygen or sulfur atoms but at least one nitrogen atom through which the heterocyclyl ring is attached to the remainder of the molecule;

$R_2$ is hydrogen, $C_1$-$C_4$-alkyl, $C_3$-$C_4$-alkenyl, $C_3$-$C_4$-alkynyl, —$CH_2OR_{16}$, —$CH_2SR_{16}$, —$C(O)R_{16}$, —$C(O)OR_{16}$, $SO_2R_{16}$, $SOR_{16}$ or $SR_{16}$ where $R_{16}$ is $C_1$-$C_8$-alkyl, $C_1$-$C_8$-alkoxyalkyl, $C_1$-$C_8$ haloalkyl or phenyl$C_1$-$C_2$-alkyl, wherein the phenyl may be substituted by up to three groups selected from halo or $C_1$-$C_4$-alkyl;

$R_3$ is hydrogen, halogen, $C_1$-$C_4$alkyl, $C_1$-$C_4$haloalkyl, $C_1$-$C_4$haloalkoxy; hydroxy, mercapto, cyano or $C_1$-$C_4$alkoxy;

$R_4$, $R_5$ and $R_6$ are independently of each other hydrogen, halogen, optionally substituted alkyl, optionally substituted alkenyl, optionally substituted alkynyl, optionally substituted aryl, optionally substituted heteroaryl, optionally substituted alkoxy, optionally substituted acyloxy, optionally substituted alkenyloxy, optionally substituted alkynyloxy, optionally substituted aryloxy, optionally substituted heteroaryloxy, optionally substituted acylamino, optionally substituted thioalkyl, $COOR_{17}$, $CONR_{18}R_{19}$, $S(O)_kR_{20}$, $SO_2NR_{21}R_{22}$, $NR_{23}R_{24}$, $NR_{25}SO_2R_{26}$, $NO_2$, CN, C(=O)$R_{27}$, C(=NOR$_{28}$)$R_{29}$ or $R_4$ and $R_5$ or $R_5$ and $R_6$ together form a five to six-membered saturated or unsaturated carbocyclic ring system or ring system or a five to six-membered heteroaromatic or heterocyclic ring system which is optionally substituted and contains one to three heteroatoms selected from O, N or S;

k is 0, 1 or 2 and $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$ and $R_{29}$ are independently H or optionally substituted alkyl or optionally substituted aryl; or a salt thereof provided that when A is CH, A' is N and $R_3$, $R_5$ and $R_6$ are all H then $R_4$ is not hydrogen, halogen, alkoxy, haloalkyl, haloalkoxy or alkyl; and that when A is CH and A' is N then $R_1$ is not an optionally substituted N-linked 5- or 6-membered heterocyclyl group containing two adjacent nitrogen atoms as the only heteroatoms in the heterocyclic ring.

2. A method according to claim 1 wherein A is CH, A' is N and j is 0.

3. A method according to claim 1 wherein $R_1$ is a) hydrazino substituted by one to three substituents independently selected from the group consisting of $C_{1-4}$alkyl, $C_{1-4}$haloalkyl, $C_{1-4}$hydroxyalkyl, $C_{1-4}$alkoxy$C_{1-4}$alkyl and $C_{1-4}$acyl;

b) cyclohexyl-amino substituted by amino;

c) piperazinyl optionally substituted by one or two $C_{1-4}$alkyl, acyl or $C_{1-4}$aminoalkyl groups;

d) morpholinyl optionally substituted by one or two $C_{1-4}$alkyl, acyl or $C_{1-4}$aminoalkyl groups; mono- or di-(lower alkyl)-amino;

e) mono- or di-(lower alkyl)-amino where the lower alkyl moieties are independently substituted by N-mono- or N,N-di-(lower alkyl)amino, (lower alkoxy)-lower alkoxy, caboxy-lower alkyl, lower alkoxy, hydroxy, hydroxy-lower alkylamino, lower alkylamino-carbonylamino or lower alkoxycarbonylamino or $C_{1-8}$alkoximino;

j) N=CR$_7$R$_8$ where $R_7$ and $R_8$ together with the carbon atom to which they are attached form a five- to seven-membered ring with 2 ring nitrogen atoms adjacent to the carbon atom double bonded to the external N atom;

k) the moiety

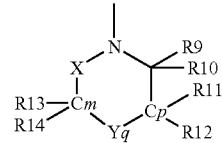

wherein the sum of (m+p) together is 0, 1, 2 or 3;

q is 0 or 1, and the sum of (m+p+q) together is 1, 2, 3 or 4;

$R_9$ is hydrogen, $C_1$-$C_6$-alkyl, $C_1$-$C_6$-haloalkyl or $C_1$-$C_6$-alkoxy;

$R_{10}$ is hydrogen, $C_1$-$C_6$-alkyl, $C_3$-$C_4$-alkenyl or $C_3$-$C_4$-alkynyl;

each of $R_{11}$, $R_{12}$, $R_{13}$ and $R_{14}$ is, independently of the others, hydrogen, $C_1$-$C_6$-alkyl, $C_1$-$C_6$-haloalkyl, hydroxy-$C_1$-$C_6$-alkyl or $C_1$-$C_6$-alkoxy-$C_1$-$C_6$-alkyl, or the ring members CR$_{13}$R14$_4$ or CR$_{11}$R$_{12}$ or CR$_9$R$_{10}$ are independently of each other a carbonyl group (C=O) or a group C=S;

X is C=O, C=S, S=O or O=S=O;

Y is O, S, C=O, CH$_2$, —N(R$_{15}$)—, —O—N(R$_{15}$)—, —N(R$_{15}$)—O— or —NH—; and $R_{15}$ is $C_1$-$C_8$-alkyl, $C_1$-$C_8$-alkoxyalkyl, $C_1$-$C_8$haloalkyl or phenyl$C_1$-$C_2$-alkyl wherein the phenyl may be substituted by up to three groups selected from halo or $C_1$-$C_4$-alkyl.

4. A method according to claim 1 wherein $R_2$ is hydrogen, $C_3$-$C_4$-alkenyl, $C_3$-$C_4$-alkynyl, —CH$_2$OR$_{16}$, CH$_2$SR$_{16}$, —C(O)R$_{16}$, —C(O)OR$_{16}$, SOR$_{16}$ or SR$_{16}$ where $R_{16}$ is as defined in claim 1.

5. A method according to claim 1 wherein $R_3$ is H, OH, halogen, methyl, ethyl, methoxy, ethoxy or CN.

6. A method according to claim 1 wherein $R_4$ is hydrogen, halogen, optionally substituted alkyl, optionally substituted alkenyl, optionally substituted alkinyl, optionally substituted alkoxy, optionally substituted alkenyloxy, optionally substituted alkynyloxy, optionally substituted thioalkyl optionally substituted aryl, COOR$_{17}$, CONR$_{18}$R$_{19}$, S(O)$_k$R$_{20}$, $SO_2NR_{21}R_{22}$ or $NR_{23}R_{24}$ where $R_{17}$, $R_{18}$, $R_{19}$, $R_{20}$, $R_{21}$, $R_{22}$, $R_{23}$ and $R_{24}$ are H or $C_{1-4}$alkyl.

7. A method according to claim 1 wherein $R_5$ is hydrogen, halogen, optionally substituted alkyl, optionally substituted alkenyl, optionally substituted alkynyl, optionally substituted alkoxy, optionally substituted alkenyloxy, optionally substituted alkynyloxy, optionally substituted thioalkyl optionally substituted aryl, $COOR_{41}$, $CONR_{42}R_{43}$, $S(O)_qR_{44}$, $SO_2NR_{45}R_{46}$ or $NR_{45a}R_{46a}$ where $R_{41}$, $R_{42}$, $R_{43}$, $R_{44}$, $R_{45}$, $R_{46}$, $R_{45a}$, $R_{46a}$, are independently H or optionally substituted alkyl.

8. A method according to claim 1 wherein $R_6$ is hydrogen, $C_1$-$C_6$alkyl or $C_1$-$C_6$haloalkyl; halogen, hydroxy, mercapto, cyano, $C_1$-$C_6$alkoxy, $C_1$-$C_6$alkylthio, amino, $C_1$-$C_6$alkylamino, di($C_1$-$C_6$alkyl)-amino, —O—CO—$R_{54}$, —NH—CO—$R_{53}$, where $R_{53}$ and $R_{54}$, are independently H or optionally substituted alkyl.

9. A method according to claim 1, wherein the phytopathogenic microorganisms are fungal organisms.

10. A compound of formula (I)

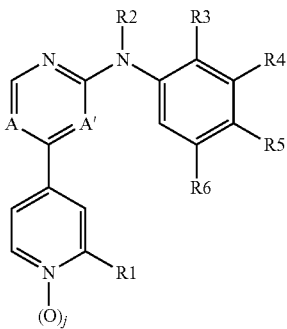

wherein
A and A' are both N or A and A' are both CH or A is CH and A' is N;
j is 0 or 1
$R_1$ is
a) hydrazino, that is unsubstituted or one- to threefold substituted by optionally substituted alkyl and/or optionally substituted acyl,
b) tetrahydro-4H-pyranyl-4-amino, pyrrolidine-3-amino, 2- or 3-tetrahydro-furylamino, all optionally substituted by amino, hydroxy, alkoxy, alkyl or alkoxyalkyl,
c) piperazinyl that is optionally substituted by amino, amino-lower alkyl, hydroxy, alkoxy, alkyl or alkoxyalkyl,
d) morpholinyl that is optionally substituted by amino, amino-lower alkyl, hydroxy, alkoxy, alkyl or alkoxyalkyl,
e) amino or mono- or di-(lower alkyl)amino wherein the lower alkyl moieties are unsubstituted or substituted by one or more substitutents independently selected from the group consisting of unsubstituted amino, N-mono- or N,N-di-(lower alkyl)-amino, (lower alkoxy)-lower alk-oxy, lower alkoxycarbonylamino, hydroxy-lower alkoxycarbonylamino, lower alkoxy-lower alkoxycarbonylamino, morpholinyl, hydroxy-lower alkylamino, cyano, halogen, oxo, hydroximino, alkoximino, optionally substituted hydrazono, lower alkenyl, lower alkynyl, guanidyl, lower alkanoylamino, hydroxy-lower alkanoylamino, lower alkoxy-lower alkanoylamino, halo-lower alkanoylamino, lower alkylaminocarbonylamino, hydroxy-lower alkylaminocarbonylamino, lower alkoxy-lower alkylaminocarbonylamino, amidino, di-lower-alkylamino-cyclohexyl, carboxy, lower alkoxycarbonyl, hydroxy-lower alkoxycarbonyl, lower alkoxy-lower alkoxycarbonyl, lower alkylcarbonyldioxy (=lower alkoxycarbonyloxy), hydroxy-lower alkoxycarbonyloxy, lower alkoxy-lower alkoxycarbonyloxy, lower alkanoyloxy, halo-lower alkanoyloxy, hydroxy-lower alkanoyloxy, lower alkoxy-lower alkanoyloxy, carbamoyl, N-mono- or N,N-di-lower alkylcarbamoyl, N-(hydroxy-lower alkyl)carbamoyl, N-lower alkyl-N-hydroxy-lower alkyl-carbamoyl, N,N-di-(hydroxy-lower alkyl)-carbamoyl, N-hydroxy-carbamoyl, hydroxy, lower alkoxy, lower alkenyloxy, lower alkinyloxy, lower haloalkoxy, lower alkylthio, lower alkylsulfoxyl, lower alkylsulfonyl, lower alkoxysilyl, 4-tetrahydro-4H-pyranyl, 3-pyrrolidinyl, 2- or 3-tetrahydrofuryl, 2- or 3-dihydrofuryl, piperazinyl, lower alkanoyl-piperazinyl, optionally substituted heteroaryl and optionally substituted heteroaryloxy,
f) optionally substituted alkanoylamino, optionally substituted alkenoylamino, optionally substituted alkynoylamino, optionally substituted mono- or di-alkylaminocarbonylamino, optionally substituted alkoxycarbonylamino, optionally substituted mono- or di-alkylaminosulfonylamino, optionally substituted mono- or di-alkylaminosulfoxylamino,
g) N-(optionally substituted alkyl)-N-(optionally substituted lower alkanoyl)-amino,
h) N-(optionally substituted alkyl)-N-(optionally substituted alkoxycarbonyl)-amino,
i) N-(optionally substituted alkyl)-N—(N',N'-mono- or di-[optionally substituted alkyl]-aminocarbonyl)-amino,
j) N=C($R_7$,$R_8$) wherein $R_7$ is hydrogen, alkyl, amino, mono- or di-alkylamino and $R_8$ is amino, mono- or dialkylamino or wherein $R_7$ and $R_8$, together with the binding carbon atom, form a saturated five- to seven-membered ring with 0, 1 or 2 ring nitrogen atoms that is optionally substituted by one or more substituents,
k) an optionally substituted 4 to 7 membered heterocyclyl group containing one or two nitrogen, oxygen or sulfur atoms but at least one nitrogen atom through which the heterocyclyl ring is attached to the remainder of the molecule;
$R_2$ is hydrogen, $C_1$-$C_4$-alkyl, $C_3$-$C_4$-alkenyl, $C_3$-$C_4$-alkynyl, —$CH_2OR_{16}$, —$CH_2SR_{16}$, —$C(O)R_{16}$, —$C(O)OR_{16}$, $SO_2R_{16}$, $SOR_{16}$ or $SR_{16}$
where $R_{16}$ is $C_1$-$C_8$-alkyl, $C_1$-$C_8$-alkoxyalkyl, $C_1$-$C_8$haloalkyl or phenyl$C_1$-$C_2$-alkyl, wherein the phenyl may be substituted by up to three groups selected from halo or $C_1$-$C_4$-alkyl;
$R_3$ is hydrogen, halogen, $C_1$-$C_4$alkyl, $C_1$-$C_4$haloalkyl, $C_1$-$C_4$haloalkoxy; hydroxy, mercapto, cyano or $C_1$-$C_4$alkoxy;
$R_4$, $R_5$ and $R_6$ are independently of each other hydrogen, halogen, optionally substituted alkyl, optionally substituted alkenyl, optionally substituted alkynyl, optionally substituted aryl, optionally substituted heteroaryl, optionally substituted alkoxy, optionally substituted acyloxy, optionally substituted alkenyloxy, optionally substituted alkynyloxy, optionally substituted aryloxy, optionally substituted heteroaryloxy, optionally substituted acylamino, optionally substituted thioalkyl, $COOR_{17}$, $CONR_{18}R_{19}$, $S(O)_kR_{20}$, $SO_2NR_{21}R_{22}$, $NR_{23}R_{24}$, $NR_{25}SO_2R_{26}$, $NO_2$, CN, $C(=O)R_{27}$, $C(=NOR_{28})R_{29}$ or $R_4$ and $R_5$ or $R_5$ and $R_6$ together form a five to six-membered saturated or unsaturated carbocyclic ring system or ring system or a five to six-membered heteroaromatic or heterocyclic ring system which is optionally substituted and contains one to three heteroatoms selected from O, N or S;

k is 0, 1 or 2 and $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$ and $R_{29}$ are independently H or optionally substituted alkyl or optionally substituted aryl; or a salt thereof provided that a) when A is CH, A' is N and $R_3$, $R_5$ and $R_6$ are all H then $R_4$ is not hydrogen, halogen, alkoxy, haloalkyl, haloalkoxy or alkyl; b) when A is CH and A' is N then $R_1$ is not an optionally substituted N-linked 5- or 6-membered heterocyclyl group containing two adjacent nitrogen atoms as the only heteroatoms in the heterocycylic ring; c) when A is CH, A' is N and $R_4$ and $R_5$ are both H then $R_3$ is not hydrogen, halogen, lower alkoxy or lower alkyl; d) when A is N, A' is N and $R_2$ is H and one of $R_3$, $R_4$, $R_5$ and $R_6$ is halogen, nitro, alkoxy, haloalkyl or haloalkoxy then $R_1$ is other than aminoalkylamino, hydroxyalkylamino, optionally substituted morpholino, optionally substituted piperidino, optionally substituted piperazino, pyridylalkylamino, alkenylamino, optionally substituted phenylamino, pyrrolidinialkylamino, and pieridinoalkylamino; e) when A is N, A' is N, and $R_5$ is OCH$_3$, R1 is not a mono-substituted lower alkylamino having the lower alkyl moiety substituted by a lower alkenyl; f) when A is N, A' is N, and $R_5$ is OCH$_3$, R1 is not a di-substituted lower alkylamino having unsubstituted lower alkyl moieties; and g) when A is N, A' is N, and $R_4$ is Cl, R1 is not a di-substituted lower alkylamino having unsubstituted lower alkyl moieties.

11. A compound according to claim 10 wherein A is CH and A' is N.

12. A compound according to claim 10 wherein $R_1$ is a) hydrazino substituted by one to three substituents independently selected from the group consisting of $C_{1-4}$alkyl, $C_{1-4}$haloalkyl, $C_{1-4}$hydroxyalkyl, $C_{1-4}$alkoxy$C_{1-4}$alkyl and $C_{1-4}$acyl;

c) piperazinyl optionally substituted by one or two $C_{1-4}$alkyl, acyl or $C_{1-4}$aminoalkyl groups;

d) morpholinyl optionally substituted by one or two $C_{1-4}$alkyl, acyl or $C_{1-4}$aminoalkyl groups; mono- or di-(lower alkyl)-amino;

e) mono- or di-(lower alkyl)-amino where the lower alkyl moieties are independently substituted by N-mono- or N,N-di-(lower alkyl)amino, (lower alkoxy)-lower alkoxy, caboxy-lower alkyl, lower alkoxy, hydroxy, hydroxy-lower alkylamino, lower alkylamino-carbonylamino or lower alkoxycarbonylamino or $C_{1-8}$alkoximino;

j) N=CR$_7$R$_8$ where R$_7$ and R$_8$ together with the carbon atom to which they are attached form a five- to seven-membered ring with 2 ring nitrogen atoms adjacent to the carbon atom double bonded to the external N atom;

k) the moiety

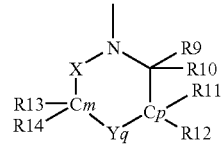

wherein the sum of (m+p) together is 0, 1, 2 or 3;

q is 0 or 1, and the sum of (m+p+q) together is 1, 2, 3 or 4;

$R_9$ is hydrogen, $C_1$-$C_6$-alkyl, $C_1$-$C_6$-haloalkyl or $C_1$-$C_6$-alkoxy;

$R_{10}$ is hydrogen, $C_1$-$C_6$-alkyl, $C_3$-$C_4$-alkenyl or $C_3$-$C_4$-alkynyl;

each of $R_{11}$, $R_{12}$, $R_{13}$ and $R_{14}$ is, independently of the others, hydrogen, $C_1$-$C_6$-alkyl, $C_1$-$C_6$-haloalkyl, hydroxy-$C_1$-$C_6$-alkyl or $C_1$-$C_6$-alkoxy-$C_1$-$C_6$-alkyl, or the ring members $CR_{13}R14_4$ or $CR_{11}R_{12}$ or $CR_9R_{10}$ are independently of each other a carbonyl group (C=O) or a group C=S;

X is C=O, C=S, S=O or O=S=O;

Y is O, S, C=O, CH$_2$, —N(R$_{15}$)—, —O—N(R$_{15}$)—, —N(R$_{15}$)—O— or —NH—; and $R_{15}$ is $C_1$-$C_8$-alkyl, $C_1$-$C_8$-alkoxyalkyl, $C_1$-$C_8$haloalkyl or phenylC$_1$-C$_2$-alkyl wherein the phenyl may be substituted by up to three groups selected from halo or $C_1$-$C_4$-alkyl.

13. A compound according to claim 10 wherein $R_2$ is hydrogen, $C_3$-$C_4$-alkenyl, $C_3$-$C_4$-alkynyl, —CH$_2$OR$_{16}$, CH$_2$SR$_{16}$, —C(O)R$_{16}$, —C(O)OR$_{16}$, SOR$_{16}$ or SR$_{16}$ where $R_{16}$ is as defined in claim 1.

14. A compound according to claim 10 where $R_3$ is H, OH, halogen, methyl, ethyl, methoxy, ethoxy or CN.

15. A compound according to claim 10 wherein $R_4$ is hydrogen, halogen, optionally substituted alkyl, optionally substituted alkenyl, optionally substituted alkinyl, optionally substituted alkoxy, optionally substituted alkenyloxy, optionally substituted alkynyloxy, optionally substituted thioalkyl optionally substituted aryl, COOR$_{17}$, CONR$_{18}$R$_{19}$, S(O)$_k$R$_{20}$, SO$_2$NR$_{21}$R$_{22}$ or NR$_{23}$R$_{24}$ where R$_{17}$, R$_{18}$, R$_{19}$, R$_{20}$, R$_{21}$, R$_{22}$, R$_{23}$ and R$_{24}$ are H or $C_{1-4}$alkyl.

16. A compound according to claim 10 wherein $R_5$ is hydrogen, halogen, optionally substituted alkyl, optionally substituted alkenyl, optionally substituted alkinyl, optionally substituted alkoxy, optionally substituted alkenyloxy, optionally substituted alkynyloxy, optionally substituted thioalkyl optionally substituted aryl, COOR$_{41}$, CONR$_{42}$R$_{43}$, S(O)$_q$R$_{44}$, SO$_2$NR$_{45}$R$_{46}$ or NR$_{45a}$R$_{46a}$ where R$_{41}$, R$_{42}$, R$_{43}$, R$_{44}$, R$_{45}$, R$_{46}$ R$_{45a}$, R$_{46a}$, are independently H or optionally substituted alkyl.

17. A compound according to claim 10 wherein $R_6$ is hydrogen, $C_1$-$C_6$alkyl or $C_1$-$C_6$haloalkyl; halogen, hydroxy, mercapto, cyano, $C_1$-$C_6$alkoxy, $C_1$-$C_6$alkylthio, amino, $C_1$-$C_6$alkylamino, di($C_1$-$C_6$alkyl)-amino, —O—CO—R$_{54}$, —NH—CO—R$_{53}$, where R$_{53}$ and R$_{54}$, are independently H or optionally substituted alkyl.

18. A composition for controlling and protecting against phytopathogenic microorganisms, comprising a compound of formula I according to claim 10 as active ingredient together with a suitable carrier.

* * * * *